US009925154B2

(12) United States Patent
Eddy et al.

(10) Patent No.: US 9,925,154 B2
(45) Date of Patent: Mar. 27, 2018

(54) CYSTEAMINE IN THE TREATMENT OF FIBROTIC DISEASE

(71) Applicant: Seattle Children's Hospital, Seattle, WA (US)

(72) Inventors: Allison A. Eddy, Seattle, WA (US); Daryl M. Okamura, Shoreline, WA (US)

(73) Assignee: Seattle Children's Hospital, Seattle, WA (US)

( * ) Notice: Subject to any disclaimer, the term of this patent is extended or adjusted under 35 U.S.C. 154(b) by 0 days.

(21) Appl. No.: 15/284,416

(22) Filed: Oct. 3, 2016

(65) Prior Publication Data

US 2017/0165207 A1 Jun. 15, 2017

Related U.S. Application Data

(63) Continuation of application No. 14/353,273, filed as application No. PCT/US2011/057935 on Oct. 26, 2011, now Pat. No. 9,468,612.

(51) Int. Cl.
*A61K 31/13* (2006.01)
*A61K 31/145* (2006.01)

(52) U.S. Cl.
CPC .................................. *A61K 31/145* (2013.01)

(58) Field of Classification Search
CPC ........................................... A61K 31/145
USPC ....................................................... 514/665
See application file for complete search history.

(56) References Cited

U.S. PATENT DOCUMENTS

| 4,816,482 | A | 3/1989 | Oiry et al. |
|---|---|---|---|
| 5,520,926 | A | 5/1996 | Ferguson |
| 5,554,655 | A | 9/1996 | Thoene |
| 5,571,714 | A | 11/1996 | Dasch et al. |
| 5,583,103 | A | 12/1996 | Ruoslahti et al. |
| 5,654,270 | A | 8/1997 | Ruoslahti et al. |
| 5,683,988 | A | 11/1997 | Chung |
| 5,693,607 | A | 12/1997 | Segarini et al. |
| 5,693,610 | A | 12/1997 | Matsunaga et al. |
| 5,705,609 | A | 1/1998 | Ruoslahti et al. |
| 5,714,519 | A | 2/1998 | Cincotta et al. |
| 5,726,149 | A | 3/1998 | Ruoslahti et al. |
| 5,772,995 | A | 6/1998 | Fakhrai et al. |
| 5,821,227 | A | 10/1998 | Dennis et al. |
| 5,821,234 | A | 10/1998 | Dzau |
| 5,824,655 | A | 10/1998 | Border |
| 5,830,847 | A | 11/1998 | Letarte et al. |
| 5,869,462 | A | 2/1999 | Dzau |
| 6,001,969 | A | 12/1999 | Lin et al. |
| 6,008,011 | A | 12/1999 | Lin et al. |
| 6,010,872 | A | 1/2000 | Lin et al. |
| 6,015,693 | A | 1/2000 | Letarte et al. |
| 6,184,226 | B1 | 2/2001 | Chakravarty et al. |
| 6,468,522 | B1 | 10/2002 | Stein et al. |
| 6,521,266 | B1 | 2/2003 | Mann |
| 8,026,284 | B2 | 9/2011 | Dohil et al. |
| 2010/0111898 | A1 | 5/2010 | Pelura |
| 2010/0303870 | A1 | 12/2010 | Dohil et al. |

FOREIGN PATENT DOCUMENTS

| EP | 0 813 875 B1 | 1/2003 |
|---|---|---|
| JP | 8-119984 | 5/1996 |
| WO | WO 91/04748 | 4/1991 |
| WO | WO 91/08291 | 6/1991 |
| WO | WO 91/10727 | 7/1991 |
| WO | WO 92/00330 | 1/1992 |
| WO | WO 93/09228 | 5/1993 |
| WO | WO 93/09800 | 5/1993 |
| WO | WO 94/09812 | 5/1994 |
| WO | WO 94/10187 | 5/1994 |
| WO | WO 94/25588 | 11/1994 |
| WO | WO 95/10610 | 4/1995 |
| WO | WO 97/13844 | 4/1997 |
| WO | WO 97/40848 | 11/1997 |
| WO | WO 98/17304 | 4/1998 |
| WO | WO 98/48024 | 10/1998 |
| WO | WO 00/66631 | 11/2000 |
| WO | WO 02/62753 | 8/2002 |
| WO | WO 02/62776 | 8/2002 |
| WO | WO 02/62787 | 8/2002 |
| WO | WO 02/62793 | 8/2002 |
| WO | WO 02/62794 | 8/2002 |
| WO | WO 02/66462 | 8/2002 |
| WO | WO 02/94833 | 11/2002 |
| WO | WO 03/87304 | 10/2003 |
| WO | WO 03/97615 | 11/2003 |
| WO | WO 03/97639 | 11/2003 |
| WO | WO 04/10929 | 2/2004 |

(Continued)

OTHER PUBLICATIONS

Eddy, et al., "Cysteamine effects on extracellular matrix accumulation in chronic kidney disease," *Cystinosis Research Foundation Progress Report*, p. 1-3, Dec. 2008.
Eddy, et al., "Cysteamine effects on extracellular matrix accumulation in chronic kidney disease," *Cystinosis Research Foundation Progress Report*, p. 1-4, Dec. 2009.
Eddy, et al., "Cysteamine effects on extracellular matrix accumulation in chronic kidney disease," *Cystinosis Research Foundation Progress Report*, p. 1-4, Jun. 2009.
Eddy, et al., "Cysteamine effects on extracellular matrix accumulation in chronic kidney disease," *Cystinosis Research Foundation Progress Report*, pp. 1-4, Jun. 2010.
Eddy, et al., "Cysteamine effects on extracellular matrix accumulation in chronic kidney disease," *Cystinosis Research Foundation Progress Report*, pp. 1-5, Dec. 2010.

(Continued)

*Primary Examiner* — Raymond J Henley, III
(74) *Attorney, Agent, or Firm* — Knobbe Martens Olson & Bear LLP

(57) ABSTRACT

Fibrotic diseases are characterized by the replacement of healthy tissue with scar tissue and extracellular matrix in response to tissue damage. Here we describe the reduction of extracellular matrix (ECM) deposition, interstitial fibroblasts, interstitial volume, expression of Collagen I mRNA and protein, expression of profibrotic cytokines and macrophage infiltration by Cysteamine treatment.

86 Claims, 22 Drawing Sheets

(56) References Cited

FOREIGN PATENT DOCUMENTS

| WO | WO 04/16606 | 2/2004 |
|---|---|---|
| WO | WO 04/21989 | 3/2004 |
| WO | WO 04/22054 | 3/2004 |
| WO | WO 04/24159 | 3/2004 |
| WO | WO 04/26302 | 4/2004 |
| WO | WO 04/26871 | 4/2004 |
| WO | WO 04/47818 | 6/2004 |
| WO | WO 04/48381 | 6/2004 |
| WO | WO 04/48382 | 6/2004 |
| WO | WO 04/48930 | 6/2004 |
| WO | WO 04/50659 | 6/2004 |
| WO | WO 04/56352 | 7/2004 |
| WO | WO 04/72033 | 8/2004 |
| WO | WO 04/87056 | 10/2004 |
| WO | WO 05/010049 | 2/2005 |
| WO | WO 05/032481 | 4/2005 |
| WO | WO 05/065691 | 7/2005 |
| WO | WO 05/092894 | 10/2005 |
| WO | WO 05/097832 | 10/2005 |
| WO | WO 05/101149 | 10/2005 |
| WO | WO 06/026305 | 3/2006 |
| WO | WO 06/026306 | 3/2006 |
| WO | WO 06/052568 | 5/2006 |
| WO | WO 06/086469 | 8/2006 |
| WO | WO 07/089670 | 8/2007 |
| WO | WO 09/070781 | 6/2009 |

OTHER PUBLICATIONS

Eddy, et al., "Cysteamine effects on extracellular matrix accumulation in chronic kidney disease," *Cystinosis Research Foundation Final Progress Report*, pp. 1-7, Jun. 2011.
File History of U.S. Appl. No. 14/353,273, filed Apr. 21, 2014.
Gahl et al., "Cystinosis," *N Engl J Med*, 347(2):111-21, 2002.
Gorelik, Leonid, and Richard A. Flavell, "Transforming growth factor-β in T-cell biology." *Nature Reviews Immunology*, 2:46-53 (2002).
International Search Report dated Mar. 1, 2012, received in PCT/US2011/057935.
Jeon, et al., "Different inhibition characteristics of intracellular transglutaminase activity by cystamine and cysteamine," *Experimental and Molecular Medicine*, vol. 36, No. 6, 576-581, Dec. 2004.
Kleta, Robert et al., "A deeper look into cysteamine absorption for the treatment of cystinosis." *The Journal of Pediatrics*, 148:718-9, 2006.
Levtchenko, Elena N., et al. "Strict cysteamine dose regimen is required to prevent nocturnal cystine accumulation in cystinosis." *Pediatr. Nephrol.* 21:110-113, 2006.
Okamura et al., "Cysteamine modulates extracellular matrix accumulation during chronic kidney injury by obstruction," *Second International Cystinosis Research Symposium*. p. 1-2, Apr. 8, 2010.
Okamura et al., "Cysteamine ameliorates progressive interstitial fibrosis by modulating oxidative stress and attenuating extracellular matrix synthesis during chronic kidney injury," Poster, American Society of Nephrology, Nov. 2010.

Overview of the key participants in the pathogensis of tubulo-interstitial fibrosis.

FIGURE 3B
Interstitial Collagen
Sham
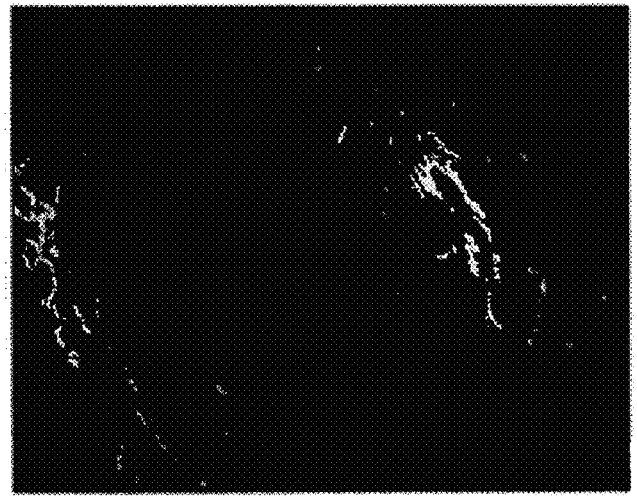
Day 14 After UUO
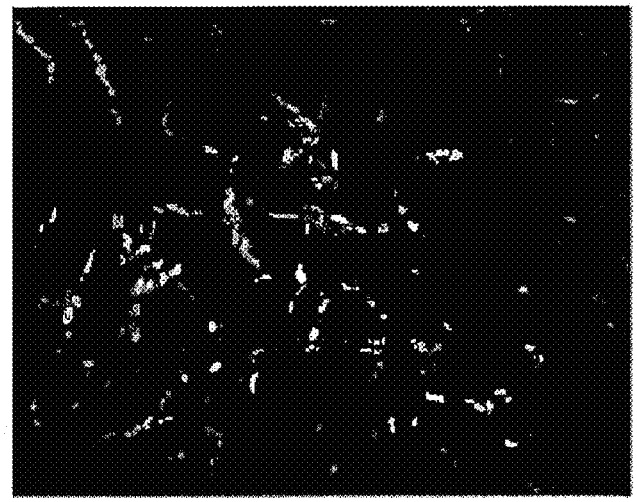

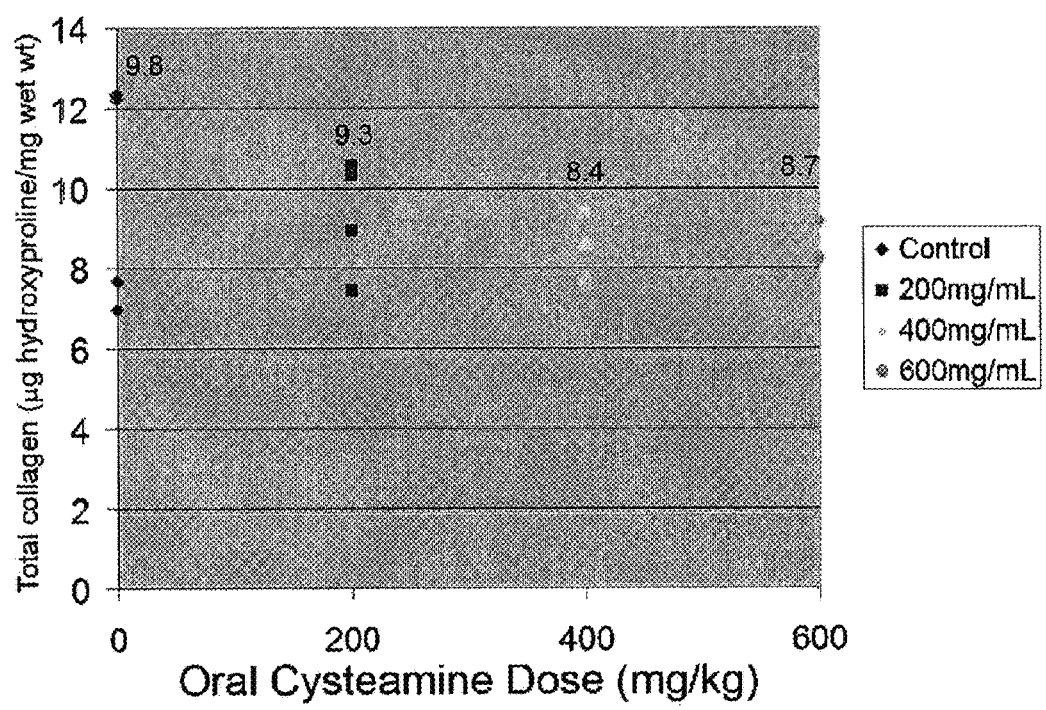

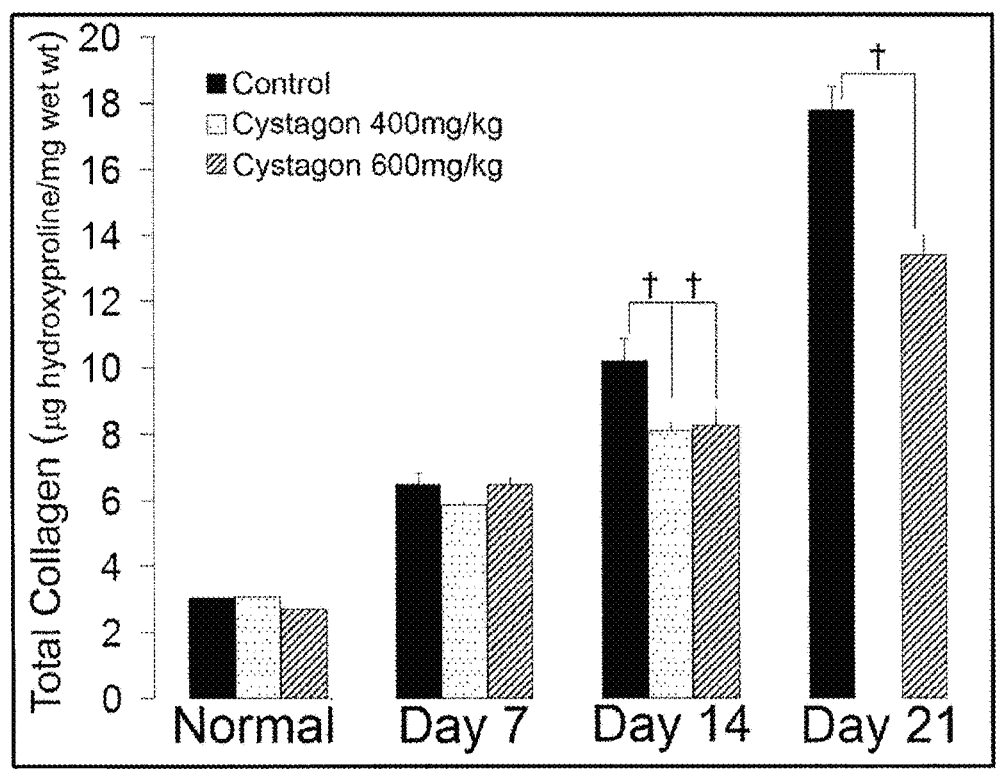

Are endogenous cysteamine levels sufficient to provide protection?

Trend toward less fibrosis in Vanin-1 null mice

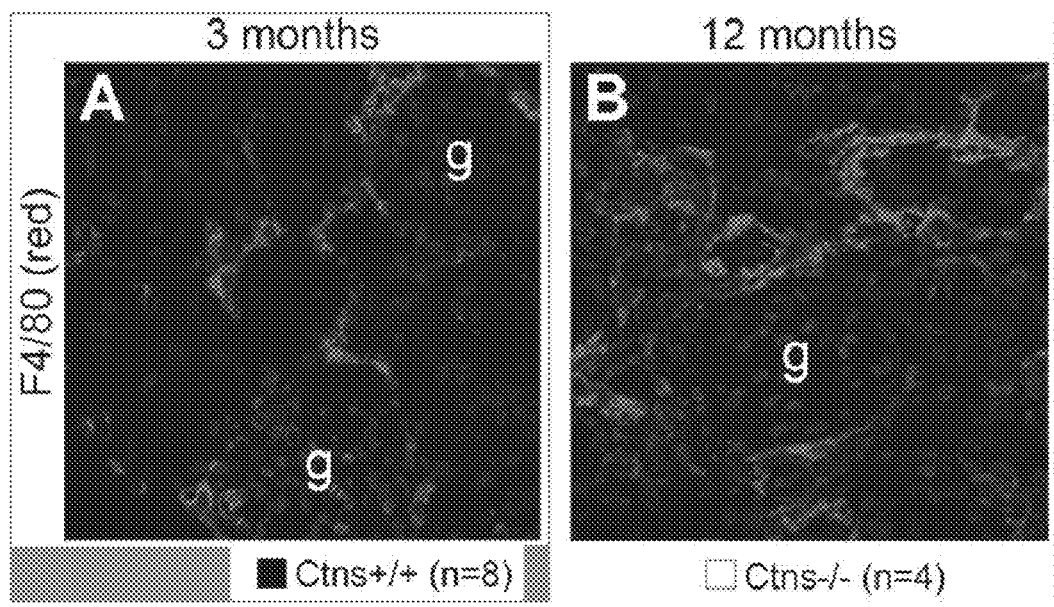
*FIG. 13A*      *FIG. 13B*
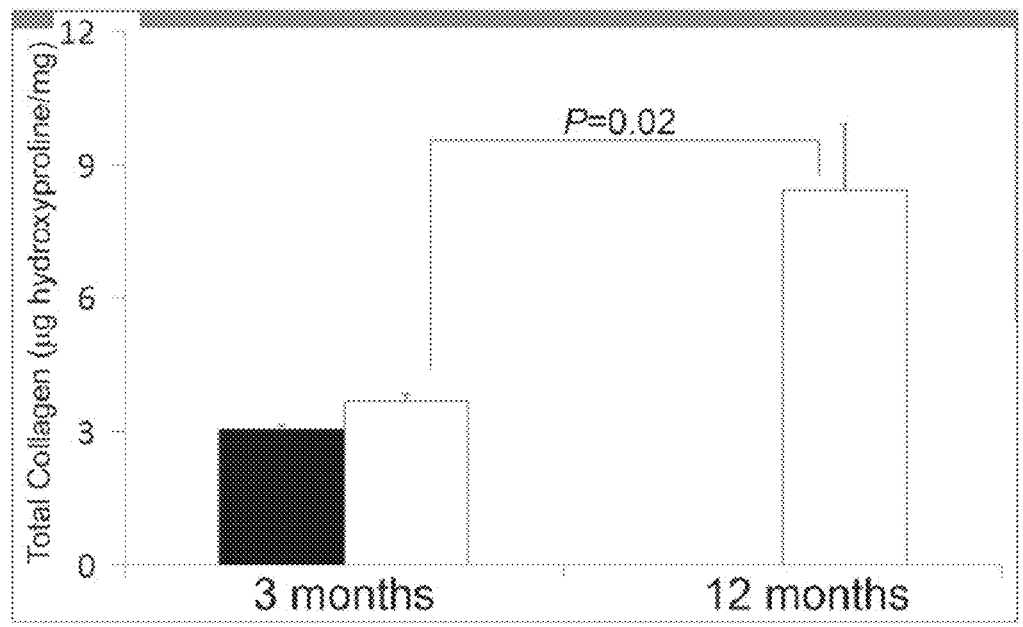
*FIG. 13C*

TGase2 is expressed in the kidney

Preliminary data

Human CKD kidney stained for ε-(γ-glutamyl lysine)

No difference in Transglutaminase

CYSTEAMINE IN THE TREATMENT OF FIBROTIC DISEASE

CROSS REFERENCE TO RELATED APPLICATIONS

This application is a continuation of and claims the benefit of priority to U.S. application Ser. No. 14/353,273, filed on Apr. 21, 2014, which claims the benefit of priority to U.S. National Phase Application of PCT International Application Number PCT/US2011/057935, filed on Oct. 26, 2011, designating the United States of America and published in the English language. The disclosures of the above-referenced applications are hereby expressly incorporated by reference in its entirety.

BACKGROUND

Field of the Invention

The present embodiments relate generally to compositions and methods for treating a patient having or being at risk for developing pathological fibrosis.

Description of the Related Art

Fibrosis can occur in the lung, liver, kidney, eye, heart, and other organs of the body. Fibrosis can be due to toxic or infectious injury, such as cigarette smoke to the lungs or viral hepatitis infection of the liver. The causes of some fibrotic diseases are currently unknown or poorly understood. Fibrosis is typically considered to be an irreversible process.

One such fibrotic disease is Chronic kidney disease (CKD), also known as chronic renal disease, which affects approximately 26 million Americans. CKD is characterized by the progressive loss of renal function over a protracted period of time (i.e., months or years). CKD leads to a buildup of fluid and waste products, which affects most body systems, including blood pressure, red blood cell production, and bone density. Complications of CKD include cardiovascular disease, anemia and pericarditis. If the progression of CKD is not halted, CKD can develop into end-Stage renal disease (ESRD), or chronic renal failure (CRF), which is a severe illness where the kidneys no longer function and the patient requires dialysis or a kidney transplant.

The most common causes of CKD are diabetes mellitus, hypertension, and glomerulonephritis, which is characterized by inflammation of the glomeruli, or small blood vessels in the kidneys. CKD is also caused by genetic disorders, such as Polycystic Kidney Disease (PKD), characterized by the growth of multiple cysts in the kidneys which reduce kidney function leading to kidney failure and Nephropathic cystinosis, a lysosomal storage disorder caused by defective transport of the amino acid cystine out of lysosomes. The stored cystine crystallizes within the lysosomes, leading to widespread tissue and organ damage. Other causes of CKD include poisons, such as the long term use of some over-the-counter medications and trauma.

There is no cure for CKD and left untreated it usually progresses. The goals of treatment are to slow disease progression, treat the underlying causes, treat complications of disease, and when necessary, replace lost kidney function. Current strategies for slowing progression and treating the underlying conditions contributing to CKD include controlling blood glucose levels, controlling high blood pressure and eating an appropriate diet. If CKD can not be controlled and progresses to kidney failure, dialysis or a kidney transplant are required.

SUMMARY

The present embodiments relate to the amelioration of progressive interstitial fibrosis by cysteamine and/or cystamine. Several embodiments relate to the amelioration of progressive interstitial fibrosis by modulating oxidative stress. Some embodiments relate to a method of reducing myofibroblast accumulation and interstitial macrophage infiltration by administering cysteamine and/or cystamine. Several embodiments relate to preventing interstitial fibrosis through the modulation of oxidative stress and profibrotic signaling within the interstitium. Some embodiments relate to the administration of cysteamine and/or cystamine to reduce oxidative stress and profibrotic signaling.

Several embodiments relate to a method of treating a fibrotic disease comprising administering, to a patient diagnosed with the disease, an effective amount of cysteamine and/or cystamine product, or a salt thereof; wherein the administration of cysteamine and/or cystamine product, or a salt thereof, results in the amelioration of the disease in the patient. In some embodiments, the fibrotic disease is atherosclerosis, asthma, cardiac fibrosis, organ transplant fibrosis, colloid and hypertrophic scar, muscle fibrosis, pancreatic fibrosis, bone-marrow fibrosis, liver fibrosis, cirrhosis of liver and gallbladder, scleroderma, pulmonary fibrosis, diffuse parenchymal lung disease, idiopathic interstitial fibrosis, interstitial pneumonitis, desquamative interstitial pneumonia, respiratory bronchiolitis, interstitial lung disease, acute interstitial pneumonitis, nonspecific interstitial pneumonia, cryptogenic organizing pneumonia, lymphocytic interstitial pneumonia, renal fibrosis, or chronic kidney disease.

Several embodiments relate to a method for treating a disorder associated with elevated levels of interstitial extracellular matrix (ECM) in an organ, said method comprising administering, to a patient diagnosed with the disorder, an effective amount of cysteamine and/or cystamine product, or a salt thereof; wherein the administration of cysteamine and/or cystamine product, or a salt thereof, results in the lowering of interstitial ECM in the organ of the patient.

Some embodiments relate to the attenuation of extracellular matrix synthesis during chronic kidney injury by cysteamine and/or cystamine product.

Several embodiments relate to methods of suppressing interstitial renal fibrosis by reducing the synthesis of extracellular matrix during chronic kidney injury by administering an effective amount of cysteamine and/or cystamine product. In some embodiments, an effective amount may be about 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, and may increase by 25 mg/kg increments up to 1000 mg/kg BW cysteamine. In some embodiments, an effective amount cysteamine and/or cystamine is a total daily dose of from approximately 0.25 g/m$^2$ to 4.0 g/m$^2$ body surface area. In some embodiments, an effective amount cysteamine is at least about a total daily dose of 0.5, 0.6, 0.7, 0.8, 0.9, 1.0, 1.1, 1.2, 1.3, 1.4, 1.5, 1.6, 1.7, 1.8, 1.9 or 2 g/m$^2$, or up to about 0.8, 0.9, 1.0, 1.1, 1.2, 1.3, 1.4, 1.5, 1.6, 1.7, 1.8, 1.9, 2.0, 2.2, 2.5, 2.7, 3.0, or 3.5 g/m$^2$.

Several embodiments relate to preventing interstitial fibrosis through the modulation of oxidative stress and profibrotic signaling within the interstitium during chronic kidney injury.

Several embodiments described herein relate to compositions and methods for delaying, slowing, or halting the progression of chronic kidney disease. Some embodiments relate to a method of delaying, slowing, or halting the progression of chronic kidney disease by cysteamine modulation of extracellular matrix accumulation.

Several embodiments described herein relate to a method for delaying, slowing or halting the progression of chronic kidney disease from Stage 1 to Stage 2, Stage 2 to Stage 3, Stage 3 to Stage 4, or Stage 4 to Stage 5 by administration of an effective amount of cysteamine and/or cystamine product. In some embodiments, an effective amount may be about 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, and may increase by 25 mg/kg increments up to 1000 mg/kg BW cysteamine and/or cystamine. In some embodiments, an effective amount cysteamine and/or cystamine is a total daily dose of from approximately 0.25 g/m$^2$ to 4.0 g/m$^2$ body surface area. In some embodiments, an effective amount cysteamine and/or cystamine is at least about a total daily dose of 0.5, 0.6, 0.7, 0.8, 0.9, 1.0, 1.1, 1.2, 1.3, 1.4, 1.5, 1.6, 1.7, 1.8, 1.9 or 2 g/m$^2$, or up to about 0.8, 0.9, 1.0, 1.1, 1.2, 1.3, 1.4, 1.5, 1.6, 1.7, 1.8, 1.9, 2.0, 2.2, 2.5, 2.7, 3.0, or 3.5 g/m$^2$.

Several embodiments relate to a method for treating renal fibrosis or chronic kidney disease comprising administering to a subject in need thereof a composition comprising a cysteamine product, optionally cysteamine or cystamine or a pharmaceutically acceptable salt thereof. In some embodiments, the chronic kidney disease is characterized by renal fibrosis, glomerulosclerosis or tubulointerstitial fibrosis, or a combination thereof. In some embodiments, the method comprises preventing chronic kidney disease, optionally wherein the subject is suffering from chronic renal insufficiency (CRI). In some embodiments, the method comprises treating a subject suffering from Stage I, II, III, IV or V chronic kidney disease. In some embodiments, the subject is suffering from nephropathy, glomerulosclerosis, glomerulonephritis, diabetes, fibrocystic kidney disease, fibrotic kidney cancer, and renal interstitial fibrosis. In some embodiments, the composition reduces extracellular matrix deposition in the kidney. In some embodiments, the composition reduces the level of one or more of collagen I, collagen II, collagen IV, procollagen I, procollagen III, or fibronectin. In some embodiments, the composition reduces myofibroblast infiltration and/or interstitial macrophage infiltration in the kidney. In some embodiments, the composition reduces fibrosis in the kidney. In some embodiments, the composition is administered less than four times/day, optionally, one, two, or three times per day. In some embodiments, the composition is administered at a dose from 0.01 mg to 1000 mg/kg per day. In some embodiments, the composition is administered at a dose from 0.25 g/m2 to 4.0 g/m2 per day. In some embodiments, the composition further comprises a pharmaceutically acceptable carrier, excipient, or diluent. In some embodiments, the composition is a sterile pharmaceutical composition. In some embodiments, the composition is administered for a period of at least 3 weeks. In some embodiments, the composition is administered for a period of at least 4 weeks, 6 weeks, 8 weeks, 12 weeks, 16 weeks, 20 weeks, or 24 weeks. In some embodiments, the composition is a delayed or controlled release dosage form that provides increased delivery of the cysteamine product to the small intestine. In some embodiments, the delayed or controlled release dosage form comprises an enteric coating that releases the cysteamine composition when the composition reaches the small intestine or a region of the gastrointestinal tract of a subject in which the pH is greater than about pH 4.5. In some embodiments, the composition is administered orally. In some embodiments, the composition is administered parenterally. In some embodiments, the composition is administered with a second agent useful to treat renal fibrosis, chronic kidney disease, or the associated disease state, optionally diabetes.

Several embodiments relate to a composition for use in the treatment of renal fibrosis or chronic kidney disease comprising a cysteamine product, optionally cysteamine or cystamine or a pharmaceutically acceptable salt thereof. In some embodiments, the composition further comprises a pharmaceutically acceptable carrier, excipient, or diluent. In some embodiments, the composition is a sterile pharmaceutical composition. In some embodiments, the composition is a delayed or controlled release dosage form that provides increased delivery of the cysteamine product to the small intestine. In some embodiments, the delayed or controlled release dosage form comprises an enteric coating that releases the cysteamine composition when the composition reaches the small intestine or a region of the gastrointestinal tract of a subject in which the pH is greater than about pH 4.5. In some embodiments, the composition comprises a second agent useful to treat renal fibrosis, chronic kidney disease, or the associated disease state, optionally diabetes.

Some embodiments relate to a method of treating CKD comprising administering an effective amount of cysteamine to a patient in need thereof. In some embodiments, an effective amount may be about 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, and may increase by 25 mg/kg increments up to 1000 mg/kg BW cysteamine. In some embodiments, an effective amount cysteamine is a total daily dose of from approximately 0.25 g/m$^2$ to 4.0 g/m$^2$ body surface area. In some embodiments, an effective amount cysteamine is at least about a total daily dose of 0.5, 0.6, 0.7, 0.8, 0.9, 1.0, 1.1, 1.2, 1.3, 1.4, 1.5, 1.6, 1.7, 1.8, 1.9 or 2 g/m$^2$, or up to about 0.8, 0.9, 1.0, 1.1, 1.2, 1.3, 1.4, 1.5, 1.6, 1.7, 1.8, 1.9, 2.0, 2.2, 2.5, 2.7, 3.0, or 3.5 g/m$^2$.

Some embodiments relate to a method of treating CKD comprising administering an effective amount of cystamine to a patient in need thereof. In some embodiments, an effective amount may be about 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, and may increase by 25 mg/kg increments up to 1000 mg/kg BW cystamine. In some embodiments, an effective amount cystamine is a total daily dose of from approximately 0.25 g/m$^2$ to 4.0 g/m$^2$ body surface area. In some embodiments, an effective amount cystamine is at least about a total daily dose of 0.5, 0.6, 0.7, 0.8, 0.9, 1.0, 1.1, 1.2, 1.3, 1.4, 1.5, 1.6, 1.7, 1.8, 1.9 or 2 g/m$^2$, or up to about 0.8, 0.9, 1.0, 1.1, 1.2, 1.3, 1.4, 1.5, 1.6, 1.7, 1.8, 1.9, 2.0, 2.2, 2.5, 2.7, 3.0, or 3.5 g/m$^2$.

Some embodiments relate to a method of treating interstitial fibrosis comprising administering an effective amount of cysteamine to a patient in need thereof. In some embodiments, an effective amount may be about 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, and may increase by 25 mg/kg increments up to 1000 mg/kg BW cysteamine. In some embodiments, an effective amount cysteamine is a total daily dose of from approximately 0.25 g/m$^2$ to 4.0 g/m$^2$ body surface area. In some embodiments, an effective amount cysteamine is at least about a total daily dose of 0.5, 0.6, 0.7, 0.8, 0.9, 1.0, 1.1, 1.2, 1.3, 1.4, 1.5, 1.6, 1.7, 1.8, 1.9 or 2 g/m$^2$, or up to about 0.8, 0.9, 1.0, 1.1, 1.2, 1.3, 1.4, 1.5, 1.6, 1.7, 1.8, 1.9, 2.0, 2.2, 2.5, 2.7, 3.0, or 3.5 g/m$^2$.

Some embodiments relate to a method of treating interstitial fibrosis comprising administering an effective amount of cystamine to a patient in need thereof. In some embodiments, an effective amount may be about 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, and may increase by 25 mg/kg increments up to 1000 mg/kg BW cystamine. In some embodiments, an effective amount cystamine is a total daily dose of from approximately 0.25 g/m$^2$ to 4.0 g/m$^2$ body surface area. In some embodiments, an effective amount cystamine is at least about a total daily dose of 0.5, 0.6, 0.7, 0.8, 0.9, 1.0, 1.1, 1.2, 1.3, 1.4, 1.5, 1.6, 1.7, 1.8, 1.9 or 2 g/m$^2$, or up to about 0.8, 0.9, 1.0, 1.1, 1.2, 1.3, 1.4, 1.5, 1.6, 1.7, 1.8, 1.9, 2.0, 2.2, 2.5, 2.7, 3.0, or 3.5 g/m$^2$.

BRIEF DESCRIPTION OF THE DRAWINGS

FIG. 3B shows a photomicrograph of interstitial collagen in a mouse kidney subjected to sham surgery (top panel) and UUO (bottom panel).

FIG. 5 shows a graph depicting total kidney collagen as measured by hydroxyproline concentration in individual mice receiving placebo, 200 mg/kg, 400 mg/kg or 600 mg/kg cysteamine bitartrate 1 added to the drinking water for 14 days after UUO.

FIG. 6 shows a graph depicting total kidney collagen as measured by hydroxyproline concentration at 0, 3, 7, 14, and 21 days after UUO in dosage groups of mice receiving placebo, 400 mg/kg or 600 mg/kg cysteamine bitartrate.

FIG. 13A shows a representative confocal image of F4/80+ interstitial macrophages in cystinotic (Ctns−/−) mouse kidneys at 3 months. FIG. 13B shows a representative confocal image of F4/80+ interstitial macrophages in cystinotic (Ctns−/−) mouse kidneys at 12 months. (g=glomeruli.) FIG. 13C shows a graph depicting total collagen in control (Ctns+/+)(n=8) and Ctns−/− (n=4) kidneys at 3 and 12 months of age.

DETAILED DESCRIPTION

Several embodiments described herein relate to the treatment of fibrosis. Fibrosis is a pathologic process, which occurs when the body's natural healing process goes awry, leading to over production of extracellular matrix (ECM) and scar formation in response to tissue damage. Fibrosis formation involves the interaction between many cell types and cytokines, and when the balance becomes profibrotic, there is fibrosis formation. There are many fibrotic diseases, including, but not limited to, atherosclerosis, asthma, cirrhosis, scleroderma, and pulmonary fibrosis. In some embodiments, the fibrosis is fibrosis of the lung, heart, blood vessel, liver, gallbladder, kidney, skin, lung, muscle, pancreas, eye, adrenal gland, thyroid, or other organs of the body.

Figure 1A:
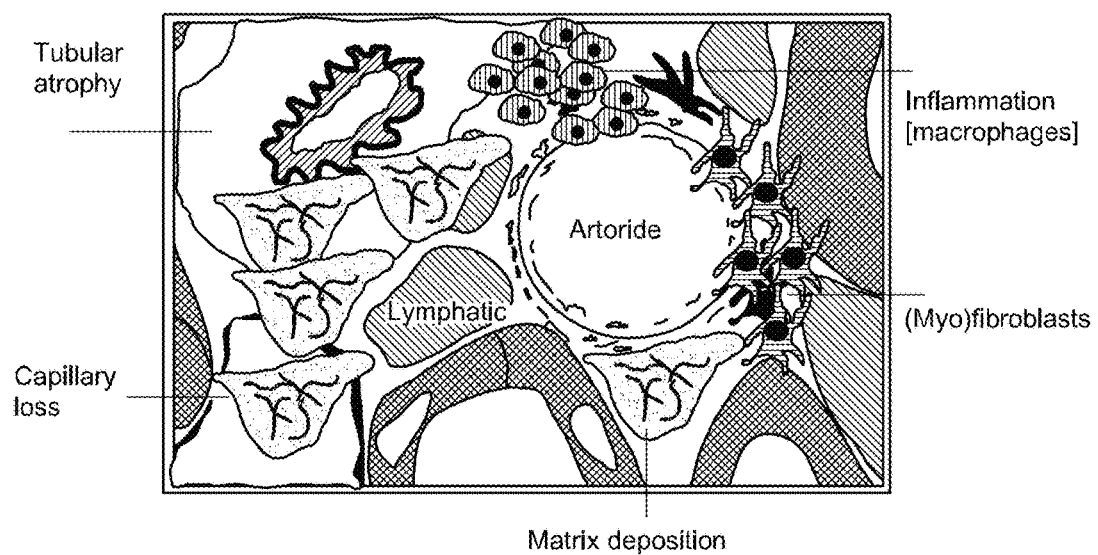
FIG. 1A shows an illustration depicting key steps in kidney scar formation.
Figure 1B:
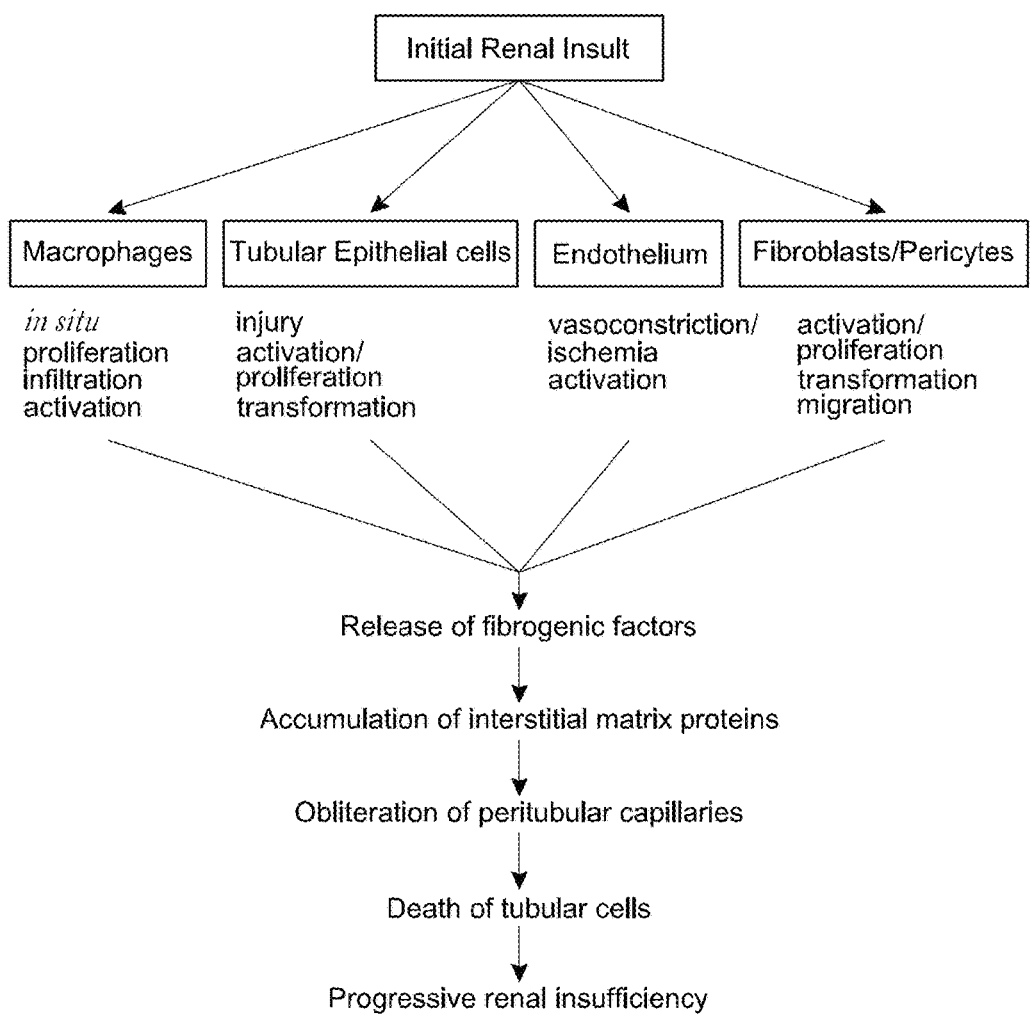
FIG. 1B shows a diagram depicting an overview of the key participants in the pathogenesis of tubulo-interstitial fibrosis.

Several embodiments relate to chronic kidney disease (CKD). CKD begins with renal injury; the progression thereafter depends upon a number of genetic and environmental factors. Periods of injury/inflammation are followed by repair processes, which may result in regeneration of renal structures and recovery of function, or may result in replacement of renal structures by nonfunctional matrices. Regardless of the cause, the underlying mechanism in the progression of chronic kidney disease to kidney failure is the accumulation of scar tissue in the kidney due to fibrosis, the formation of excess fibrous connective tissue. Although it is not known what triggers fibrosis as opposed to functional repair, renal fibrosis is characterized by the loss of renal tubules and peritubular capillaries, inflammation (macrophage infiltration), accumulation of extracellular matrix proteins and the presence of myofibroblasts in the interstitial space. A depiction of key steps in kidney scar formation is shown in FIGS. 1A and 1B. The area occupied by the tubules declines as the interstitial area increases. Tubular loss explains the close relationship between interstitial fibrosis and declining renal function. As shown in FIG. 1D, reduced renal function as measured by inulin clearance is tightly correlated with interstitial disease score.

The cellular events of renal fibrosis occur simultaneously, and often in a mutually stimulating manner. These events include increased matrix production, inhibition of matrix degradation, modulation of matrix receptors to facilitate cell-matrix interactions, release of fibrogenic factors, fibroblast activation, interstitial myofibroblast recruitment, tubular epithelial-to-mesenchymal transition, monocytic and lymphocytic cell infiltration, and cell apoptosis. The result is the replacement of normal structures with accumulated extracellular matrix (ECM). A summary of matrix proteins that accumulate in the interstitium during renal fibrosis is shown at Table 1.

TABLE 1

Matrix proteins that accumulate in the interstitium during renal fibrosis

Interstitial matrix proteins

Collagens I, III, V, VII, XV
Fibronectin
Tenascin
Basement membrane proteins

Collagen IV
Laminin
Extracellular proteoglycans

Large chondroitin sulfate proteoglycans (aggrecan, versican)
Small proteoglycans (decorin, fibromodulin, biglycan)
Basement membrane proteoglycans (heparin sulfate proteoglycan, perlecan)
Polysaccharides and glycoproteins Hyaluronan
Thrombospondin
Secreted protein, acidic, and rich in cysteine (SPARC)

CKD is classified into five stages of increasing severity. Stage 1 is characterized by slightly diminished function, kidney damage with normal or relatively high glomerular filtration rate (GFR) (≥90 mL/min/1.73 m$^2$). Stage 2 is characterized by a mild reduction in GFR (60-89 mL/min/1.73 m$^2$) with kidney damage. Kidney damage is defined as pathological abnormalities or markers of damage, including abnormalities in blood or urine tests or imaging studies. Stage 3 is characterized by a moderate reduction in GFR (30-59 mL/min/1.73 m$^2$). Stage 4 is characterized by severe reduction in GFR (15-29 ml/min/1.73 m$^2$). Stage 5, which is also known as established kidney failure, is characterized by GFR<15 mL/min/1.73 m$^2$ and permanent renal replacement therapy (RRT) is required. Patients with chronic kidney disease stages 1-3 are generally asymptomatic, while clinical manifestations typically appear in stages 4-5. The goal of therapy is to slow down or halt the progression of CKD to Stage 5.

Figure 1C:
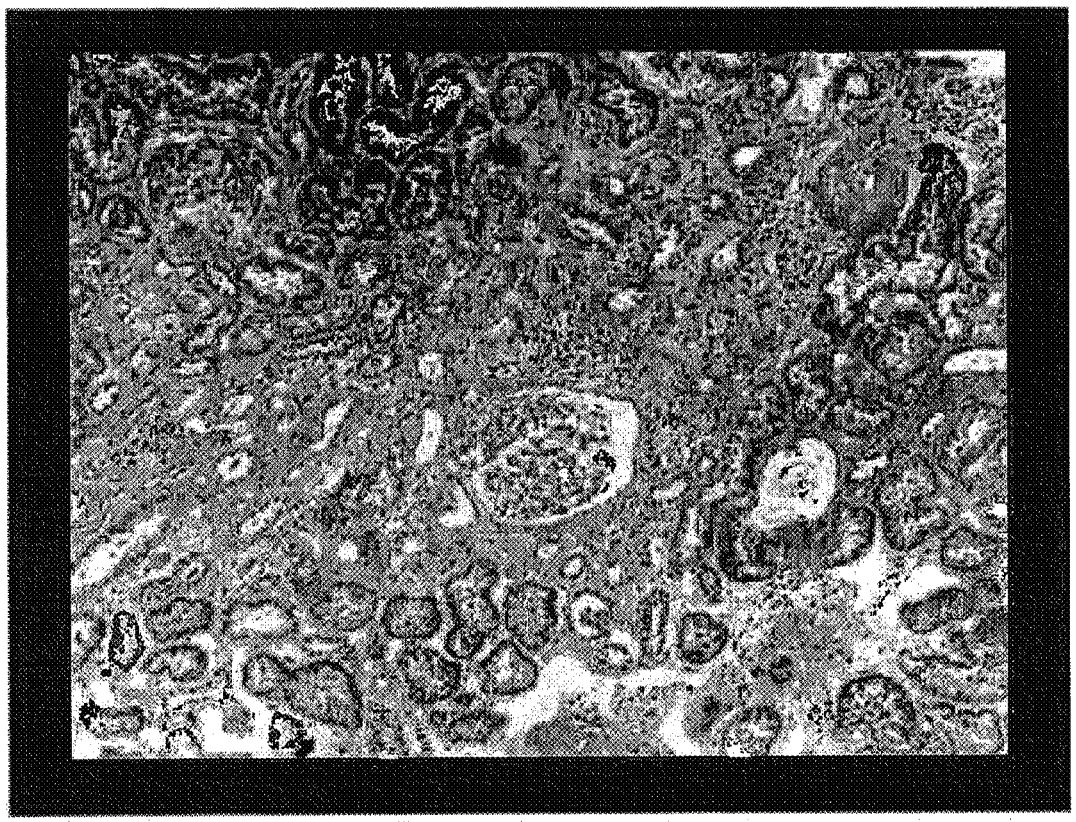
FIG. 1C shows a photomicrograph of renal interstitial fibrosis.
Figure 1D:
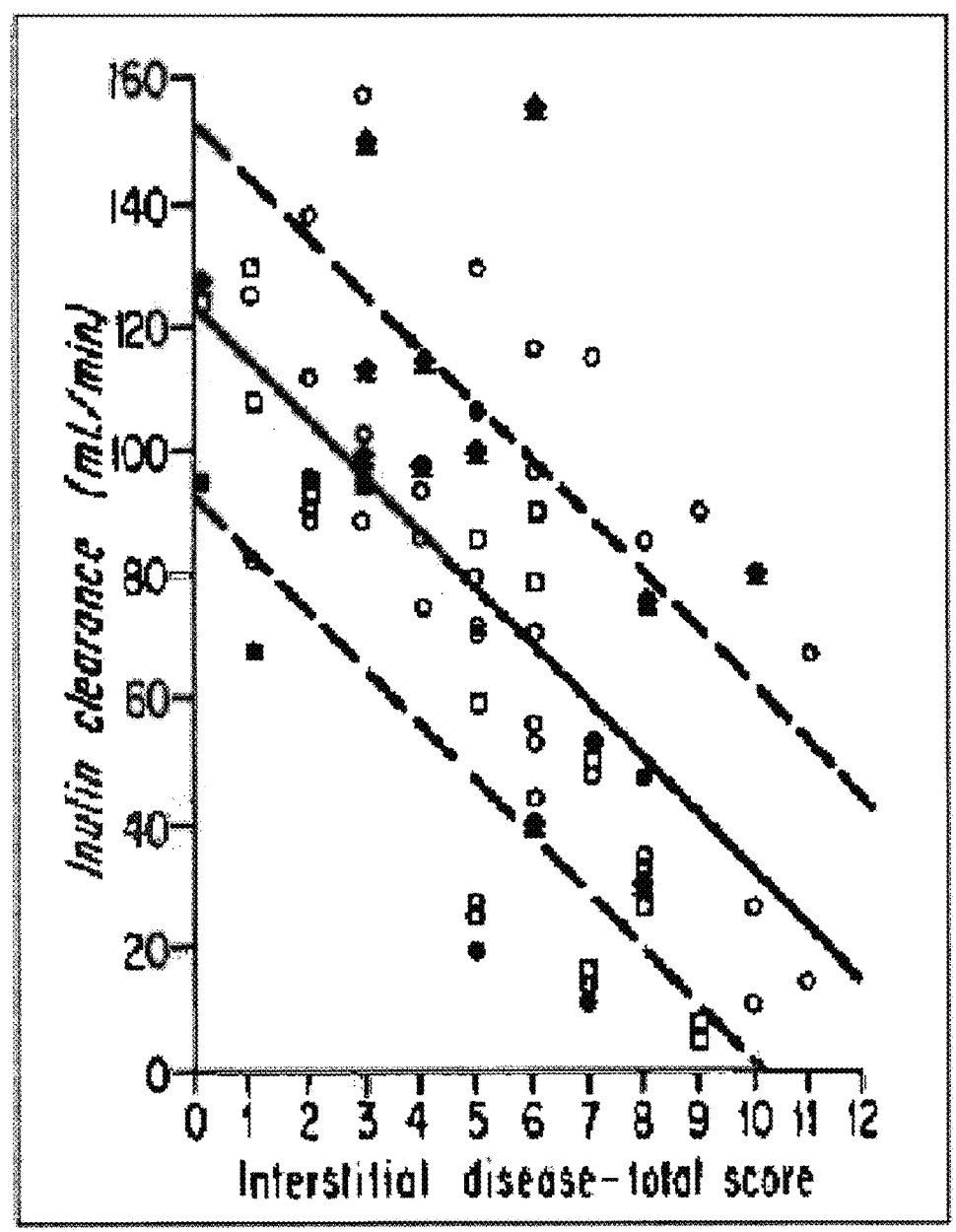
FIG. 1D shows a graph depicting the correlation between renal function as measured by inulin clearance and interstitial disease score.

Reduction in renal function is correlated with the severity of tubulointerstitial fibrosis as shown in FIG. 1C. Accordingly, slowing or stopping ECM build-up and the loss of normal kidney structures associated with interstitial renal fibrosis is likely to slow or halt the progression of CKD. However, few therapeutic options exist to slow or halt the relentless expansion of interstitial extracellular matrix (ECM) leading to nephron loss and progressive decline of kidney function. Described herein are the therapeutic effects of cysteamine on ameliorating interstitial fibrosis and the progression of CKD.

Figure 2:
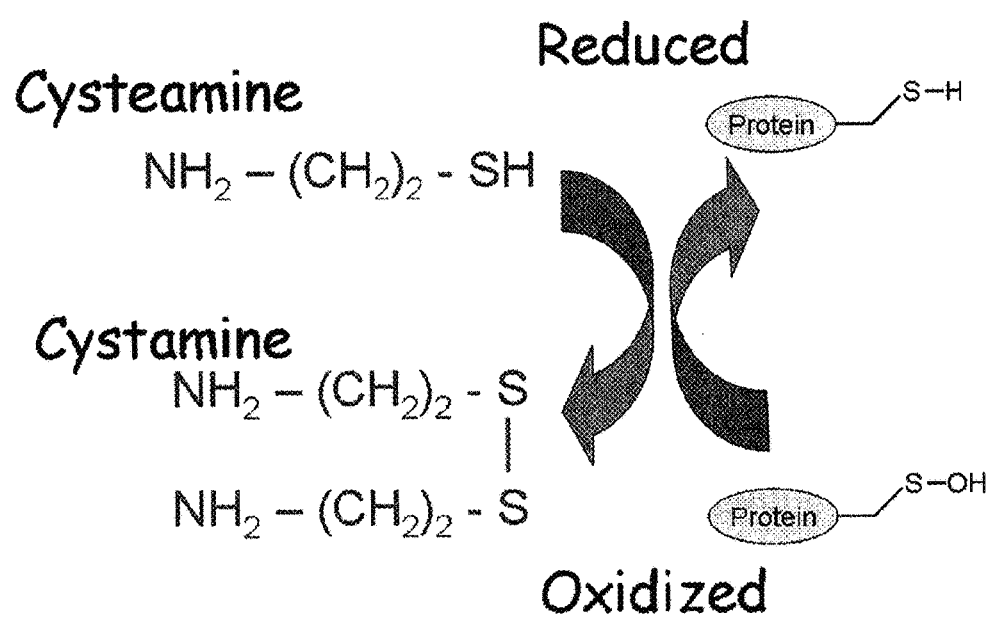
FIG. 2 depicts a diagram illustrating a putative model of the in vivo biology of cysteamine

Cysteamine plays a role in the generation of the protein glutathione (GSH), and is currently FDA approved for use in the treatment of cystinosis, an intra-lysosomal cystine storage disorder. Cystinosis is a rare inherited disorder caused by the inability to metabolize the amino acid cystine, which accumulates as cystine crystals throughout the body. These crystals cause tissue damage, particularly in the kidney. In cystinosis, cysteamine acts by converting cystine to cysteine and cysteine-cysteamine mixed disulfide which are then both able to leave the lysosome through the cysteine and lysine transporters respectively (Gahl et al., N Engl J Med 2002; 347(2):111-21). See FIG. 2. Within the cytosol the mixed disulfide can be reduced by its reaction with glutathione and the cysteine released can be used for further GSH synthesis. The synthesis of GSH from cysteine is catalyzed by two enzymes, gamma-glutamylcysteine synthetase and GSH synthetase. This pathway occurs in almost all cell types, with the liver being the major producer and exporter of GSH. The reduced cysteine-cysteamine mixed disulfide will also release cysteamine, which, in theory is then able to re-enter the lysosome, bind more cystine and repeat the process (Dohil et al., J Pediatr 2006; 148(6):764-9). In a recent study in children with cystinosis, enteral administration of cysteamine resulted in increased plasma cysteamine levels, which subsequently caused prolonged efficacy in the lowering of leukocyte cystine levels (Dohil et al., J Pediatr 2006; 148(6):764-9). This may have been due to "re-cycling" of cysteamine when adequate amounts of drug reached the lysosome. If cysteamine acts in this fashion, then GSH production may also be significantly enhanced.

Cysteamine is a potent gastric acid-secretagogue that has been used in laboratory animals to induce duodenal ulceration; studies in humans and animals have shown that cysteamine-induced gastric acid hypersecretion is most likely mediated through hypergastrinemia. In previous studies performed in children with cystinosis who suffered regular upper gastrointestinal symptoms, a single oral dose of cysteamine (11-23 mg/kg) was shown to cause hypergastrinemia and a 2 to 3-fold rise in gastric acid-hypersecretion, and a 50% rise in serum gastrin levels. Symptoms suffered by these individuals included abdominal pain, heartburn, nausea, vomiting, and anorexia. U.S. patent application Ser. No. 11/990,869 and published International Publication No. WO 2007/089670, both claiming priority to U.S. Provisional Patent Application No. 60/762,715, filed Jan. 26, 2006, (all of which are incorporated by reference herein in their entirety) showed that cysteamine induced hypergastrinemia arises, in part, as a local effect on the gastric antral-predominant G-cells in susceptible individuals. The data also suggest that this is also a systemic effect of gastrin release by cysteamine.

Subjects with cystinosis are required to ingest oral bitartrate salt of cysteamine (known commercially as CYSTA-GON®) every 6 hours day and night. When taken regularly, cysteamine can deplete intracellular cystine by up to 90% (as measured in circulating white blood cells), and this had been shown to reduce the rate of progression to kidney failure/transplantation and also to obviate the need for thyroid replacement therapy. Because of the difficulty in taking CYSTAGON®, reducing the required dosing improves the adherence to therapeutic regimen. International Publication No. WO 2007/089670 demonstrates that delivery of cysteamine to the small intestine reduces gastric distress and ulceration, increases Cmax and increases area under the curve (AUC). Delivery of cysteamine into the small intestine is useful due to improved absorption rates from the small intestine, and/or less cysteamine undergoing hepatic first pass elimination when absorbed through the small intestine. A decrease in leukocyte cystine was observed within an hour of treatment.

Cysteamine has other important metabolic effects that may provide renoprotective properties. For example, cysteamine reduces functions as an antioxidant as a biological thiol, which may impact fibrotic pathways.

Figure 3A:
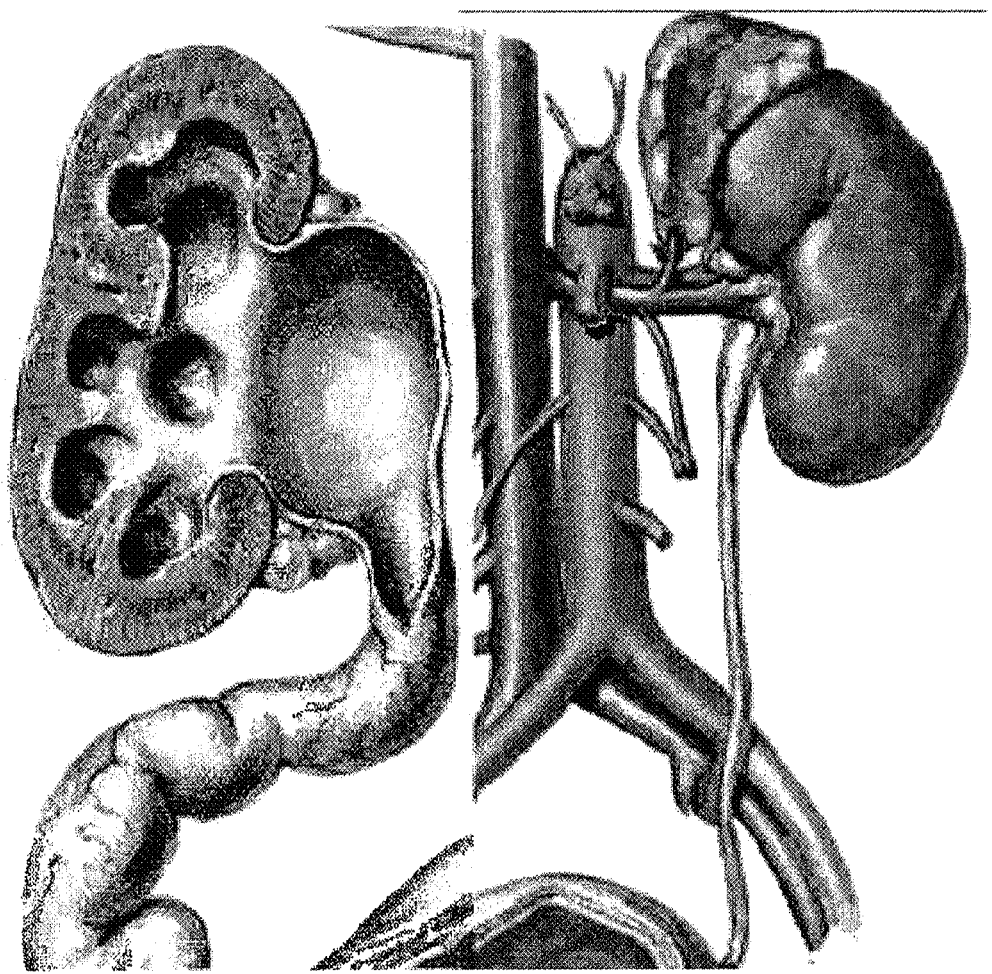
FIG. 3A shows an illustration of a kidney subject to unilateral ureteral obstruction (UUO) (left) and a normal kidney (right).

The effect of cysteamine on the degree of renal fibrosis was investigated in a model of experimental unilateral ureteral obstruction (UUO). UUO is a well-characterized experimental model of renal injury, leading to tubulointerstitial fibrosis, which is a common characteristic of many chronic nephropathies. Markers of fibrosis, such as ECM deposition, interstitial fibroblasts, interstitial volume, mRNA and protein expression for collagen I, and macrophage infiltration are all increased in the kidneys of UUO animals, making the UUO model a good experimental system for studying fibrotic diseases. FIG. 3B shows an increase in interstitial collagen in kidneys subjected to UUO.

Figure 7A:
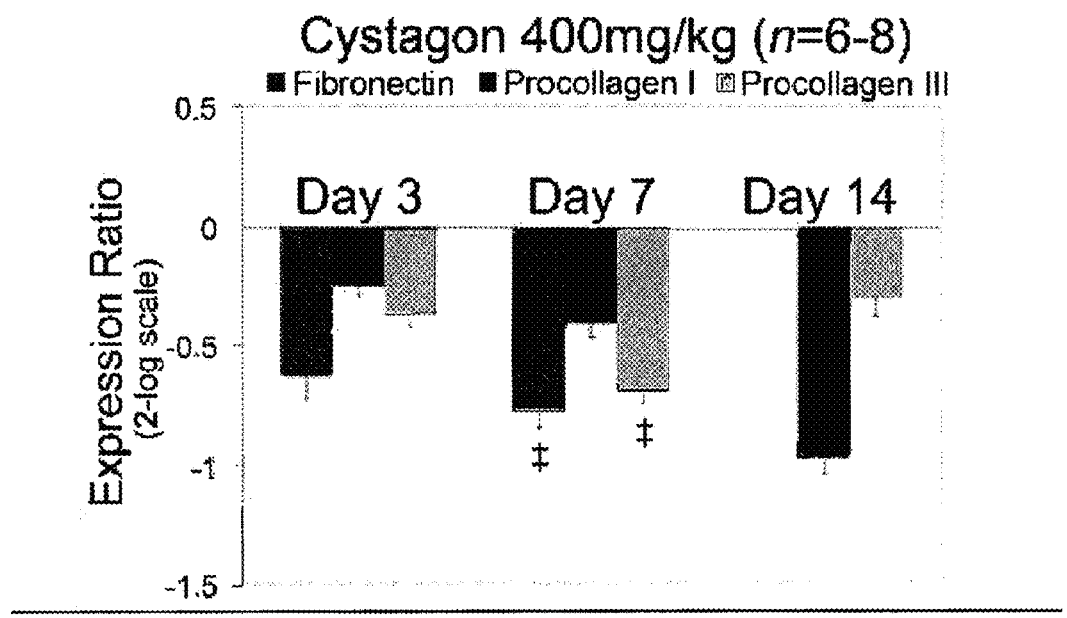
FIG. 7A shows a graph depicting the expression ratio of Fibronectin, Procollagen I and Procollagen III in kidneys of 400 mg/kg cysteamine bitartrate treated mice 3, 7 and 14 days after UUO.
Figure 7B:
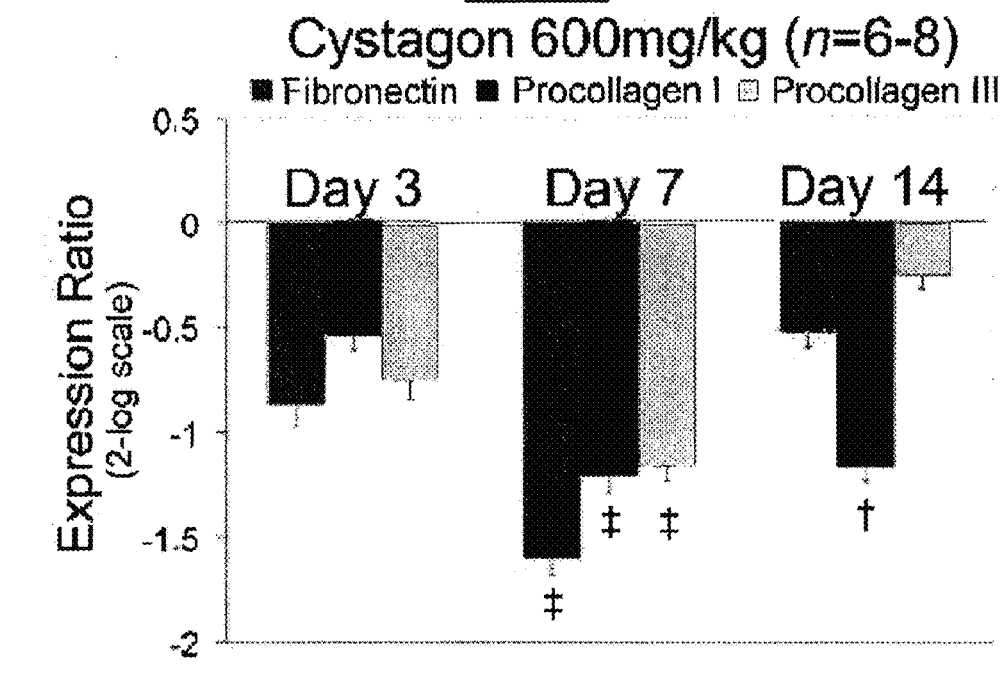
FIG. 7B shows a graph depicting the expression ratio of Fibronectin, Procollagen I and Procollagen III in kidneys of 600 mg/kg cysteamine bitartrate treated mice 3, 7 and 14 days after UUO.
Figure 8A:
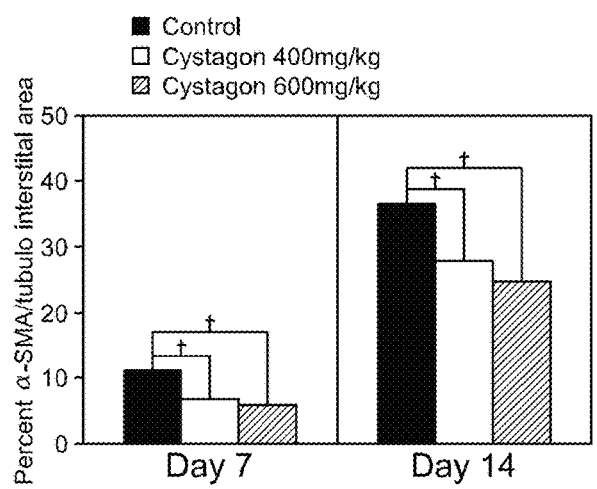
FIG. 8A shows a graph depicting α-SMA interstitial staining area 7 and 14 days after UUO in untreated mice and mice treated with 400 mg/kg or 600 mg/kg cysteamine bitartrate.
Figure 8B:
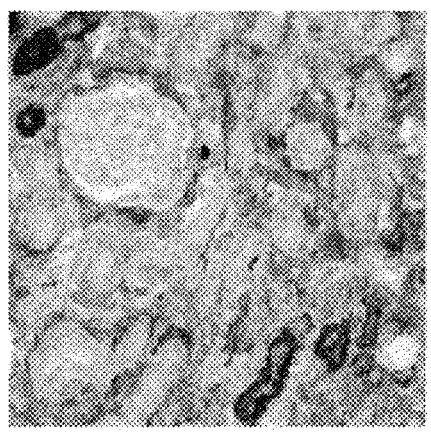
FIG. 8B shows an α-SMA immunohistochemical photomicrograph (400×) of a kidney of an untreated mouse 14 days after UUO.
Figure 8C:
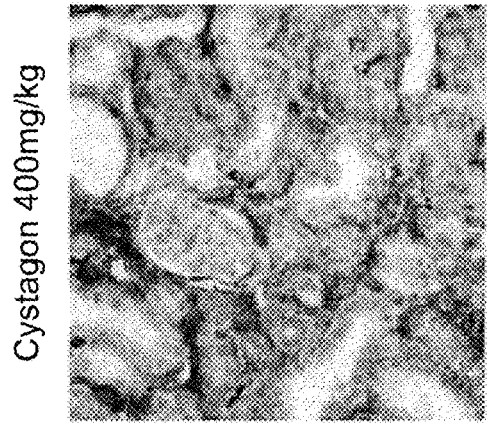
FIG. 8C shows an α-SMA immunohistochemical photomicrograph (400×) of a kidney 14 days after UUO of a mouse receiving 400 mg/kg cysteamine bitartrate.
Figure 8D:
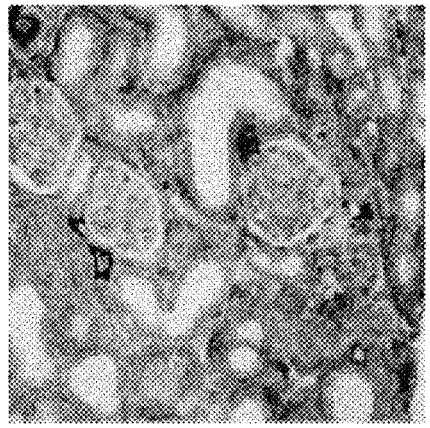
FIG. 8D shows an α-SMA immunohistochemical photomicrograph (400×) of a kidney 14 days after UUO of a mouse receiving 600 mg/kg cysteamine bitartrate.
Figure 9A:
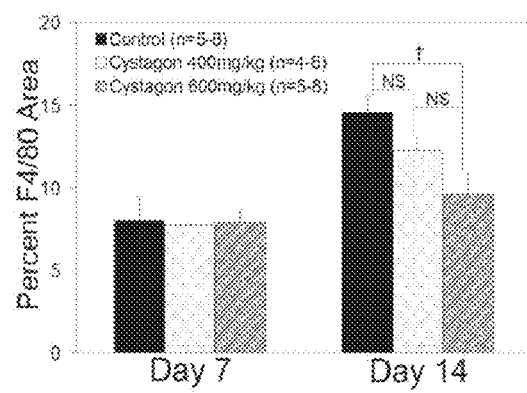
FIG. 9A shows a graph depicting F4/80-positive interstitial area 7 and 14 days after UUO in untreated mice and mice treated with 400 mg/kg or 600 mg/kg cysteamine bitartrate (n=4-8/group, †P<0.01).
Figure 9B:
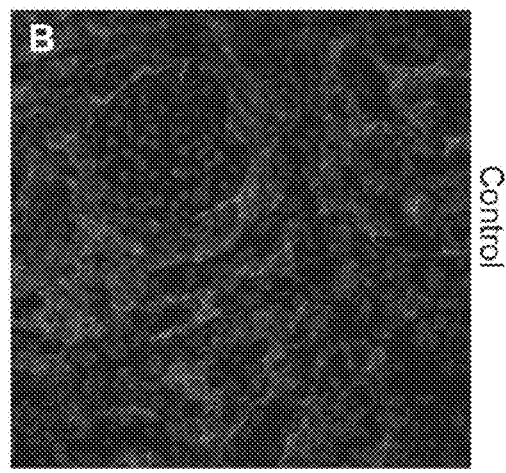
FIG. 9B shows a representative confocal (400×) image of F4/80-positive macrophages in a kidney of an untreated mouse 14 days after UUO.
Figure 9C:
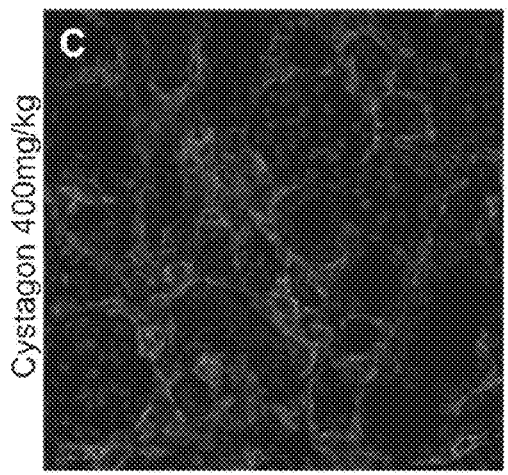
FIG. 9C shows a representative confocal (400×) image of F4/80-positive macrophages in a kidney 14 days after UUO of a mouse receiving 400 mg/kg cysteamine bitartrate.
Figure 9D:
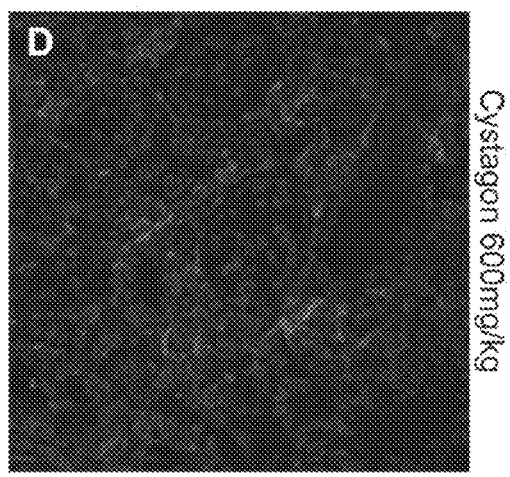
FIG. 9D shows a representative confocal (400×) image of F4/80-positive macrophages in a kidney 14 days after UUO of a mouse receiving 600 mg/kg cysteamine bitartrate.

The effect of cysteamine on the degree of renal fibrosis in UUO was investigated using two doses of cysteamine bitartrate, 400 mg/kg/day and 600 mg/kg/day and compared to mice that received vehicle alone (n=8/timepoint). Cysteamine bitartrate, the bitartrate salt of cysteamine is known commercially as Cystagon®. In these investigations of cysteamine's effect on fibrosis, mice were subjected to UUO on Day 0 and the kidneys were removed for histological assessment of fibrosis at days 3, 7, 14 and 21. Both doses were well-tolerated and measured serum levels of cysteamine were appropriate. Using loss of the renal tubular cell adherens junction protein E-cadherin as a marker of the degree of tubular damage, immunoblotting studies demonstrated that E-cadherin levels were increased 1.3 fold in the cysteamine bitartrate-treated UUO mice. Further, total kidney collagen content, as a measure of fibrosis severity, was significantly reduced by 21% in both the 400 mg/kg and 600 mg/kg doses in cysteamine-treated mice at day 14. See FIG. 6. ECM gene transcription levels were significantly down-regulated in UUO kidneys of cysteamine-treated mice: procollagen I mRNA levels were 56% lower in the mice treated with 600 mg/kg at day 14; and at day 7, despite no difference in total collagen, there was a nearly 40% reduction in kidney fibronectin and procollagen III mRNA levels in mice treated with 400 mg/kg and a nearly 60% reduction in fibronectin, procollagen I and procollagen III at higher doses of cysteamine (600 mg/kg). See FIGS. 7A and 7B. Thus cysteamine treatment reduces fibrosis severity in part by lowering the expression of ECM components after renal injury.

Myofibroblasts are the primary interstitial cells that produce extracellular matrix during chronic kidney injury as shown in FIG. 8A to 8D. Myofibroblasts can be distinguished by expression of alpha-smooth muscle actin (SMA). There was a significant reduction in alpha-SMA positive myofibroblasts by nearly 30% in both doses at day 14 in cysteamine-treated mice. See FIG. 9A to 9D. In addition, there was a significant reduction in interstitial macrophage infiltration by 34% in mice treated with 600 mg/kg/day. See FIG. 9A to 9D. These data show that cysteamine bitartrate affects both myofibroblast accumulation and interstitial macrophage infiltration.

Renal failure is accompanied by oxidative stress, which is caused by enhanced production of reactive oxygen species and impaired antioxidant defense. Oxidative stress enhances macrophage recruitment into vascular and renal lesions by increasing the responsiveness of macrophages to chemoattractants. Cysteamine, which can act as a biological antioxidant due to its thiol converting properties, may provide renal protective effects that can be attributed in part to its role as an antioxidant. Total kidney thiol content, a measure of antioxidant status, was significantly increased by 36% in high dose cysteamine-treated mice (600 mg/kg) compared to controls, indicating that cysteamine modulates antioxidant status at early time points. These data show that cysteamine affects both myofibroblast accumulation and interstitial macrophage infiltration in association with reduced oxidative stress within the interstitium during chronic kidney injury.

Figure 10A:
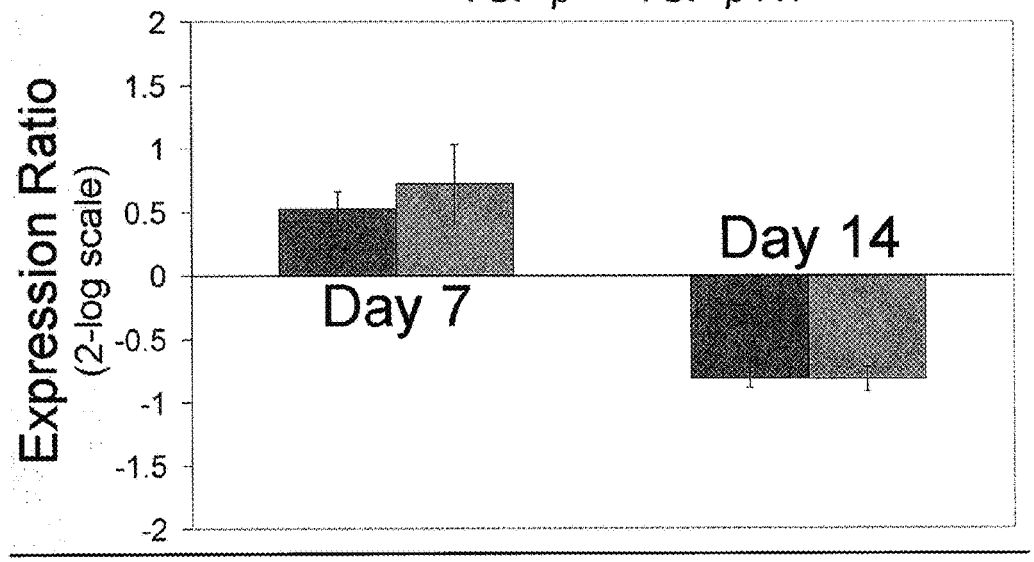
FIG. 10A shows a graph depicting relative mRNA transcription of TGF-β and TGF-β receptor 1 genes in 400 mg/kg cysteamine bitartrate-treated and control mice 7 and 14 days after UUO.
Figure 10B:
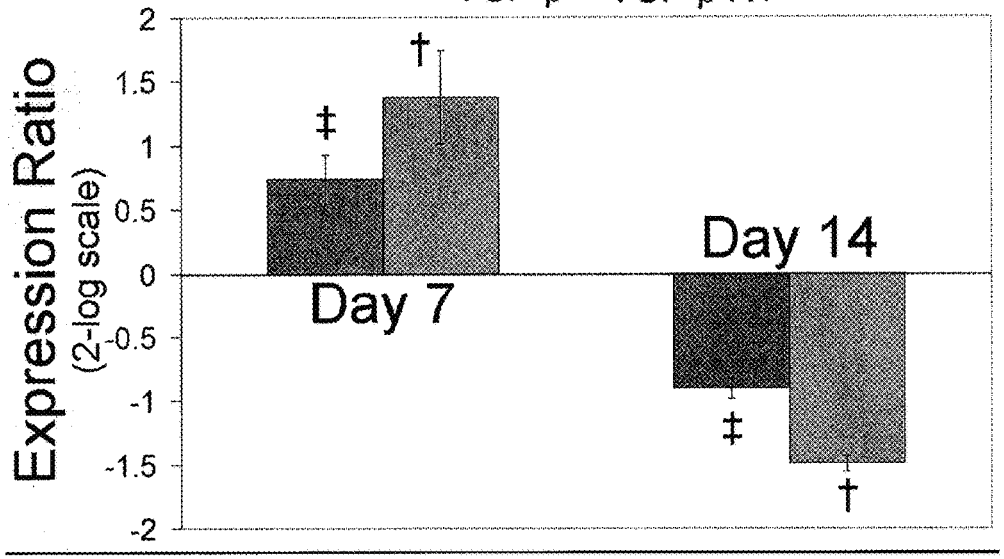
FIG. 10B shows a graph depicting relative mRNA transcription of TGF-β and TGF-β receptor 1 genes in 600 mg/kg cysteamine bitartrate-treated and control mice 7 and 14 days after UUO.

Expression of profibrotic cytokines, such as transforming growth factor β (TGF-β) and its receptor (TGF-β R1) are increased in renal fibrosis. Further, activation of TGF-β signaling induces renal fibrosis leading to end Stage kidney disease. As shown in FIGS. 10A and 10B and Table 2, cysteamine treatment decreases the expression of profibrotic cytokines in UUO kidneys. Accordingly, cysteamine asserts its renal-protective affects, in part, by inhibiting the expression of the profibrotic cytokines, TGF-β, and TGF-β R1.

Figure 12A:
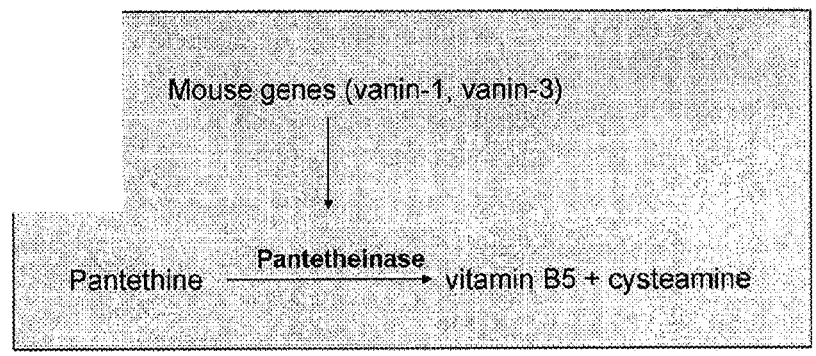
FIG. 12A depicts the metabolic pathway through which pantethine is converted to vitamin B5 and cysteamine.
Figure 12B:
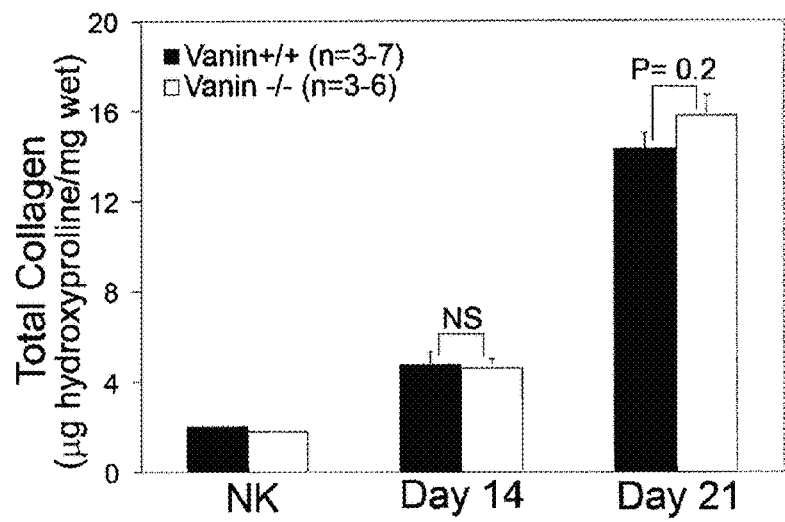
FIG. 12B shows a graph depicting total kidney collagen as measured by hydroxyproline concentration in Vanin+/+ and Vanin−/− control mice and Vanin+/+ and Vanin−/− mice 14 and 21 days after UUO.

Cysteamine is endogenously produced by the hydrolosis of pantathine into cysteamine and pantothenic acid (vitamin $B_5$). See FIG. 12A. Vanin-1 is an epithelial enzyme with pantetheinase activity which catalyzes the metabolism of pantathine. Vanin-1 is highly expressed in the kidney. Mice lacking Vanin-1 have decreased/absent cysteamine levels in epithelial cells. As shown in FIG. 12B, studies on vanin−/− mice demonstrated that there was a non-statistically significant, increase in total collagen compared to littermate control mice (P=0.2) at day 21 after UUO.

Figure 18A:
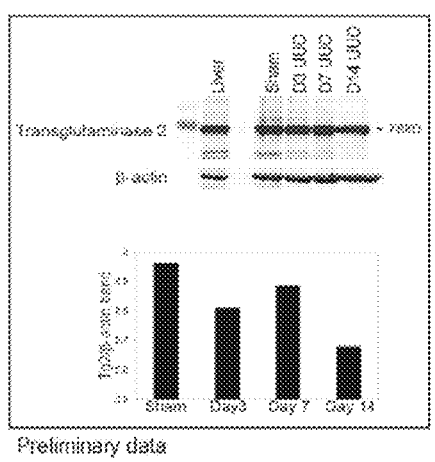
FIG. 18A shows Transglutaminase 2 (TGase2) and β-actin protein expression in mouse liver, normal kidney and UUO kidneys at days 3, 7 and 14.
Figure 18B:
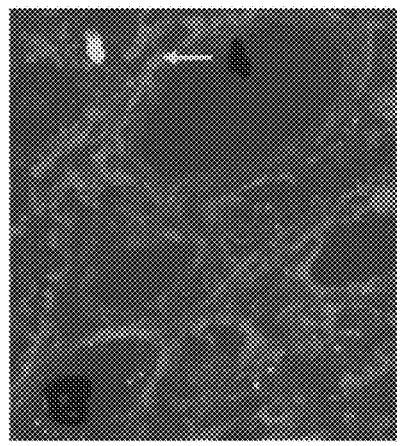
FIG. 18B shows a graph depicting TGase2 protein levels normalized to β-actin.
Figure 18C:
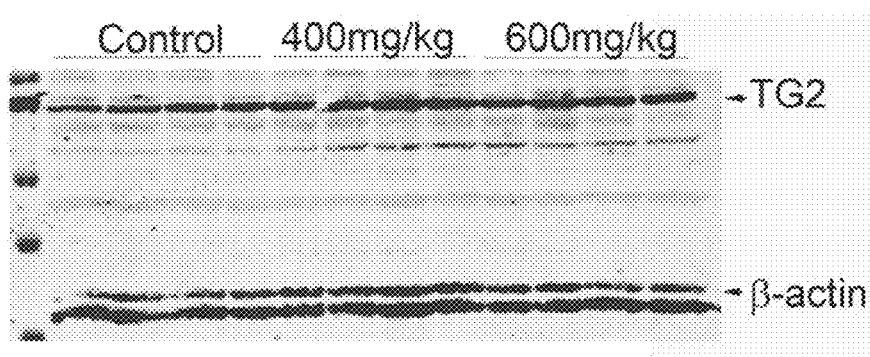
FIG. 18C shows TGase2 and β-actin protein expression in UUO kidneys of untreated mice and mice treated with 400 mg/kg or 600 mg/kg Cystagon®.

Transglutaminases (TGases) are a family of enzymes that catalyze the transamidation reaction between the γ-carboxyamide of a peptide-bound glutamine residue and the ϵ-amino group of a peptide-bound lysine residue or the primary amine group of a polyamine via forming a thioester acylenzyme intermediate at the active site cysteine. Thus, TGase activity produces cross-linked proteins or amine conjugates. One type of TGase, TGase2, acts to cross link ECM proteins, particularly Collagen III. Cross linking renders proteins resistant to degradation, which is thought to result in accelerated matrix deposition. As shown in FIG. 18A, TGase2 is expressed both in the normal and in the UUO kidney. Cystamine (β,β'-diaminodiethyl disulfide), a thiolamine joined by a disulfide bridge between two cysteamines (β-mercaptoethylamine), can act as a TGase2 inhibitor. It has been reported that cystamine may act as a TGase inhibitor due to the presence of the of the disulfide bond (Jeon et al., Exp. Mol. Med. 2004; 36(6):576-81). Cysteamine is the reduced form of cystamine, and has been speculated to have anti-fibrotic activity as an inhibitor of TGase2. Cysteamine, however, has been shown to be a less potent inhibitor of TGase than both cystamine and primary amines in vitro (Jeon et al., Exp. Mol. Med. 2004; 36(6):576-81). Additionally, no difference in TGase2 protein expression is observed in UUO kidneys treated with 400 mg/kg or 600 mg/kg cysteamine See FIG. 18C. Thus, inhibition of matrix cross-linking by inhibition of TGase2 is unlikely to be a major factor in the protection of renal function by cysteamine, and the role of cysteamine in inhibiting TGase2 in fibrosis remains unclear.

As shown herein, cysteamine treatment studies establish cysteamine's significant anti-fibrotic effects. Cysteamine treatment decreases the transcription of ECM genes in response to tissue damage. Cysteamine treatment reduces interstitial collagen deposition in models of fibrosis and decreases myofibroblast and macrophage accumulation. Accordingly, cysteamine treatment reduces the severity of fibrosis associated with tissue damage. There is no evidence, however, that cysteamine asserts its anti-fibrotic effects through TGase2 modulation.

Reduction of fibrosis by administration of cysteamine presents a treatment for a wide range of fibrotic diseases. Several embodiments described herein relate to a pharmaceutical composition comprising cysteamine or any pharmaceutically acceptable salts, analogs, derivatives, conjugates, and metabolites thereof. Several embodiments described herein relate to a pharmaceutical composition comprising prodrugs of cysteamine that can, for example, be readily metabolized in the body to produce cysteamine.

As used herein, the term "patient" refers to the recipient of a therapeutic treatment and includes all organisms within the kingdom animalia. In preferred embodiments, the animal is within the family of mammals, such as humans, bovine, ovine, porcine, feline, buffalo, canine, goat, equine, donkey, deer, and primates. The most preferred animal is human.

As used herein, the term "treat" or any variation thereof (e.g., treatment, treating, etc.), refers to any treatment of a patient diagnosed with a biological condition, such as renal interstitial fibrosis, atherosclerosis, asthma, cardiac fibrosis, organ transplant fibrosis, colloid and hypertrophic scar, bone-marrow fibrosis, liver fibrosis, cirrhosis of liver and gallbladder, scleroderma pulmonary fibrosis, Diffuse parenchymal lung disease, idiopathic interstitial fibrosis, interstitial pneumonitis, desquamative interstitial pneumonia, respiratory bronchiolitis interstitial lung disease, acute interstitial pneumonitis, nonspecific interstitial pneumonia, cryptogenic organizing pneumonia, lymphocytic interstitial pneumonia, renal fibrosis, and/or chronic kidney disease, using the materials and/or methods of the invention. The term treat, as used herein, includes: (i) preventing or delaying the presentation of symptoms associated with the biological condition of interest in an at-risk patient who has yet to display symptoms associated with the biological condition (e.g., preventing the presentation of symptoms in a patient who is suffering from chronic kidney disease stages 1-3, preventing organ transplant fibrosis, etc.); (ii) ameliorating the symptoms associated with the biological condition of interest in a patient diagnosed with the biological condition (e.g., eliminating fluid accumulation in a patient suffering from chronic kidney disease); (iii) preventing, delaying, or ameliorating the presentation of symptoms associated with complications, conditions, or diseases associated with the biological condition of interest (e.g., preventing, delaying or ameliorating the presentation of cardiovascular disease, anemia, hypertension and/or renal osteodystrophy) in either an at-risk patient or a patient diagnosed with the biological condition; (iv) slowing, delaying or halting the progression of the biological condition (e.g., slowing, delaying or halting the progression of chronic kidney disease from Stage 1 to Stage 2, Stage 2 to Stage 3, Stage 3 to Stage 4, or Stage 4 to Stage 5; delaying, slowing or halting the progression of liver fibrosis to cirrhosis; etc.); (v) preventing, delaying, slowing, halting or ameliorating the cellular events of fibrosis (e.g., preventing, delaying, slowing, halting or ameliorating increased matrix production, inhibition of matrix degradation, modulation of matrix receptors to facilitate cell-matrix interactions, fibroblast activation, epithelial-to-mesenchymal transition, monocytic and lymphocytic cell infiltration, and/or cell apoptosis); (vi) reducing interstitial disease score; (vii) preventing, delaying, ameliorating, slowing, halting or reducing myofibroblast accumulation and/or interstitial macrophage infiltration; (viii) preventing, delaying, ameliorating, slowing, halting or reducing ECM gene transcription; (ix) preventing, slowing, halting or delaying the development of chronic kidney disease in at risk patients; and/or (x) augmenting patient renal activity (e.g., enhancing glomerular filtration rate).

The term "symptom(s)" as used herein, refers to common signs or indications that a patient is suffering from a specific condition or disease. For example, chronic kidney disease-related symptoms contemplated herein include, but are not limited to, reduced glomerular filtration rate; kidney damage; presence of protein, red and white blood cells, bacteria, crystals and/or casts in urine; accumulation of interstitial macrophages, ECM accumulation; loss of nephrons; need to urinate frequently; increased water retention (puffiness or swelling) in the legs, around the eyes, or in other parts of the body; high blood pressure; anemia; loss of appetite, nausea and vomiting; itching; easy bruising; pale skin; shortness of breath from fluid accumulation in the lungs; headaches; peripheral neuropathy; altered mental status (encephalopathy from the accumulation of waste products or uremic poisons); chest pain due to pericarditis; bleeding (due to poor blood clotting); bone pain and fractures; and abnormalities in kidney size. Pulmonary fibrosis-related symptoms contemplated herein include, but are not limited to, dry unexplained cough, shortness of breath, and diminished exercise tolerance. Liver fibrosis-related symptoms contemplated herein include, but are not limited to, yellowing of the skin (jaundice), fatigue, weakness, loss of appetite, itching, and bruising.

The term "effective amount," as used herein, refers to the amount necessary to elicit the desired biological response. In accordance with the present embodiments, an effective amount of a cysteamine and/or cystamine product is the amount necessary to provide an observable effect in at least one biological factor (e.g., improvement in glomerular filtration rate, improvement in cardiac output, improvement in blood oxygen level, etc.) for use in treating a biological condition (such as cirrhosis, pulmonary fibrosis, scleroderma, chronic kidney disease, etc.). In one embodiment, an effective amount of a cysteamine and/or cystamine product is the amount necessary to prevent, slow, halt, or reduce progressive interstitial fibrosis in response to organ damage. In some embodiments, an effective amount delays, slows, halts or reduces the rate of accumulation of ECM and/or ECM gene transcription in an organ or tissue of a patient. The effective amount may include the amount necessary to delay, slow, or halt the progression of pulmonary fibrosis, liver fibrosis, organ transplant fibrosis, and/or cardiac fibrosis. In some embodiments, an effective amount delays, slows, halts or reduces the rate of loss of organ function. In some embodiments, an effective amount delays, slows or halts the progression of CKD, improving glomerular filtration rate, reducing, delaying slowing, halting or preventing interstitial fibrosis in response to kidney injury, reducing, delaying slowing, halting or preventing ECM accumulation or interstitial macrophage infiltration in the kidney, and/or reducing, delaying slowing, halting or preventing symptoms associated with CKD. In some embodiments, the effective amount may include the amount necessary to delay, slow, or halt the progression of chronic kidney disease from Stage 1 to Stage 2, Stage 2 to Stage 3, Stage 3 to Stage 4, or Stage 4 to Stage 5. In certain embodiments, the effective amount enables a 5%, 10%, 20%, 25%, 30%, 35%, 40%, 45%, 50%, 55%, 60%, 65%, 70%, 75%, 80%, 85%, 90%, 95%, 98%, 99%, and 100% decrease in severity of complications associated with the biological condition (e.g., cardiovascular disease, anemia, hypertension and/or renal osteodystrophy, etc.). In some embodiments, an effective amount delays, slows, or halts the progression of pulmonary fibrosis, reducing, delaying slowing, halting or preventing ECM accumulation, reducing, slowing or halting the appearance of bullae, delaying, halting, or slowing reduction in diffusing capacity.

As used herein, reference to a "cysteamine product" includes cysteamine, the various cysteamine salts, which include pharmaceutically acceptable salts of a cysteamine product, as well as prodrugs of cysteamine that can, for example, be readily metabolized in the body to produce cysteamine. Also included within the scope of the present embodiments are esters, amides, alkylated compounds, phosphorylated compounds, sulfated compounds, analogs, derivatives, conjugates, and metabolites of cysteamine, which have the ability as described herein to ameliorate progressive interstitial fibrosis and/or to delay, slow or halt the progression of CKD. Also included within the scope of the present embodiments are chemically modified forms cysteamine by such techniques as labeling (e.g., with radionuclides or various enzymes), or covalent polymer attachment such as pegylation (derivatization with polyethylene glycol) or mixtures thereof. Various analogs, derivatives, conjugates, and metabolites of cysteamine are well known and readily used by those skilled in the art and include, for example, compounds, compositions and methods of delivery as set forth in U.S. Pat. Nos. 6,521,266; 6,468,522; 5,714,519; and 5,554,655 the disclosures of which are herein incorporated by reference in their entirety. The disclosure is not limited with respect to a specific cysteamine salt or ester or derivative. In some embodiments, cysteamine products include, but are not limited to, hydrochloride salts, bitartrate salts, phosphorylated derivatives, and sulfated derivatives. Examples of other cysteamine products include 2-aminopropane thiol-1, 1-aminopropane thiol-2, N- and S-substituted cysteamine, AET, aminoalkyl derivatives, phosphorothioate, amifostine (U.S. Pat. No. 4,816,482). In one embodiment, a cysteamine product specifically excludes N-acetylcysteine. In one embodiment, a cysteamine product specifically includes cystamine. In another embodiment, a cysteamine product specifically excludes cystamine As further contemplated herein, the advantages of cysteamine, as set forth herein, can be achieved by promoting the endogenous production of cysteamine through natural metabolic process such as through the action of coenzyme A or as a metabolite of cysteine. This can be achieved by, for example, the administration of pantothenic acid. Pantothenic acid is a naturally occurring vitamin that is converted in mammals to coenzyme A, a substance vital to many physiological reactions. Cysteamine is a component of coenzyme A, thus increasing coenzyme A levels can result in increased levels of circulating cysteamine. Alkali metal salts, such as magnesium phosphate tribasic and magnesium sulphite (Epsom salts), enhance formation of coenzyme A. Furthermore, breakdown of coenzyme A to cysteamine is enhanced by the presence of a reducing agent, such as citric acid. Thus, the combination of pantothenic acid and alkali metal salts results in increased coenzyme A production and, concomitantly, cysteamine.

As used herein, reference to a "cystamine product" includes cystamine, the various cystamine salts, which include pharmaceutically acceptable salts of a cystamine product, as well as prodrugs of cystamine that can, for example, be readily metabolized in the body to produce cystamine. Also included within the scope of the present embodiments are esters, amides, alkylated compounds, phosphorylated compounds, sulfated compounds, analogs, derivatives, conjugates, and metabolites of cystamine, which have the ability as described herein to ameliorate progressive interstitial fibrosis and/or to delay, slow or halt the progression of CKD. Also included within the scope of the present embodiments are chemically modified forms cystamine by such techniques as labeling (e.g., with radionuclides or various enzymes), or covalent polymer attachment such as pegylation (derivatization with polyethylene glycol) or mixtures thereof. Various analogs, derivatives, conjugates, and metabolites of cystamine are well known and readily used by those skilled in the art. The disclosure is not limited with respect to a specific cystamine salt or ester or derivative. In some embodiments, cystamine products include, but are not limited to, hydrochloride salts, bitartrate salts, phosphorylated derivatives, and sulfated derivatives. In one embodiment, a cystamine product specifically excludes N-acetylcysteine. In one embodiment, a cystamine product specifically includes cysteamine. In another embodiment, a cystamine product specifically excludes cysteamine.

The term "pharmaceutically acceptable salt," as used herein, refers to any salt of a cysteamine and/or cystamine product that is pharmaceutically acceptable and does not greatly reduce or inhibit the activity of the cysteamine and/or cystamine product. Suitable examples include acid addition salts, with an organic or inorganic acid such as acetate, tartrate, trifluoroacetate, lactate, maleate, fumarate, citrate, methane, sulfonate, sulfate, phosphate, nitrate, or chloride.

For human applications, an effective amount of a cysteamine and/or cystamine product of the present embodiments is used, optionally in combination with a pharmaceutically acceptable carrier. The composition may be dry, or it may be a solution. Treatment may be reactive, for combating or preventing progression of an existing disease, or prophylactic, for preventing kidney damage in an organism susceptible to disease.

Several embodiments relate to a method of ameliorating progressive interstitial fibrosis in a mammal, comprising administering to the mammal, for example a human, an effective amount of cysteamine and/or cystamine product. Several embodiments relate to a method of delaying, slowing, or halting the progression of CKD in a mammal, comprising administering to the mammal, for example a human, an effective amount of cysteamine and/or cystamine product. Several embodiments relate to a method of improving glomerular filtration rate in a mammal, comprising administering to the mammal, for example a human, an effective amount of cysteamine and/or cystamine product. Several embodiments relate to a method of improving liver function in a mammal, comprising administering to the mammal, for example a human, an effective amount of cysteamine and/or cystamine product. Some embodiments relate to a method of improving cardiac output in a mammal, comprising administering to the mammal, for example a human, an effective amount of cysteamine and/or cystamine product.

The cysteamine and/or cystamine product is administered in a therapeutically effective amount; typically, the composition is in unit dosage form. The amount of cysteamine and/or cystamine product administered is dependent on the age, weight, and general condition of the subject, the severity of the condition being treated, and may be determined by the treating physician.

Suitable therapeutic amounts will be known to those skilled in the art and/or are described in the pertinent reference texts and literature. Current doses of cysteamine used to treat cystinosis are about 1.35 g/m2 body surface area and are generally administered 4-times per day (Levtchenko et al., Pediatr Nephrol. 21:110-113, 2006). In some embodiments, a daily dose of about 0.01 mg to 1000 mg/kg body weight (BW) of a cysteamine and/or cystamine, or an equivalent molar quantity of a cysteamine and/or cystamine, is administered to an adult patient to elicit a desired response. In one aspect, the dose is administered either one time per day or multiple times per day. In some embodiments, cysteamine and/or cystamine may be administered one, two or three or four or five times per day. In some embodiments, a daily dose of about 10 mg to about 50 mg/kg BW of a cysteamine and/or cystamine product, or an equivalent molar quantity of a cysteamine and/or cystamine product, is administered to an adult patient to elicit a desired response. In some embodiments, an effective dose may be about 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, and may increase by 25 mg/kg increments up to 1000 mg/kg BW, or may range between any two of the foregoing values. In some embodiments, about 100 mg to 2 g of cysteamine and/or cystamine, or an equivalent molar quantity thereof, is administered daily to an adult patient to elicit a desired response. In some embodiments, cysteamine and/or cystamine is administered at a total daily dose of from approximately 0.25 $g/m^2$ to 4.0 $g/m^2$ body surface area. In some embodiments, a dose is administered twice per day at about 0.5-1.0 $g/m^2$ (e.g., 0.7-0.8 $g/m^2$) body surface area. In some embodiments, at least about 0.5, 0.6, 0.7, 0.8, 0.9, 1.0, 1.1, 1.2, 1.3, 1.4, 1.5, 1.6, 1.7, 1.8, 1.9 or 2 $g/m^2$, or up to about 0.8, 0.9, 1.0, 1.1, 1.2, 1.3, 1.4, 1.5, 1.6, 1.7, 1.8, 1.9, 2.0, 2.2, 2.5, 2.7, 3.0, or 3.5 $g/m^2$ may be administered at a total daily dose. In some embodiments, cysteamine and/or cystamine may be administered at a total daily dose of about 1-1.5 $g/m^2$ body surface area, or 0.5-1 g/m2 body surface area, or about 0.7-0.8 $g/m^2$ body surface area, or about 1.35 $g/m^2$ body surface area. In some embodiments, doses of about 1.35 $g/m^2$ body surface area and are administered 4-5 times per day. Salts or esters of the same active ingredient may vary in molecular weight depending on the type and weight of the salt or ester moiety. In some embodiments, the daily dose is administered in multiple divided doses. In some embodiments, administration may continue for at least 1 day, 5 days, 7 days, 14 days, 21 days, 1 month, 3 months, 6 months, 9 months, 1 year, 2 years, or more.

In some embodiments, ½ to ⅛ of a maintenance dose of cysteamine and/or cystamine is administered to a patient initially and then the dose is gradually increased until the maintenance dose is reached. In some embodiments, a maintenance dose of 1.30 grams/m²/day of cysteamine and/or cystamine is administered in two, three, four, or five divided doses. In some embodiments, a maintenance dose of 2.0 grams/day is administered in two, three, four, or five divided doses.

For administration of the dosage form, e.g., a tablet or capsule or other oral dosage form comprising the enterically coated cysteamine and/or cystamine product, a total weight in the range of approximately 100 mg to 1000 mg is used. In exemplary embodiments, the dosage form is orally administered to a patient suffering from kidney disease. Administration may continue for at least 3 weeks, 4 weeks, 6 weeks, 8 weeks, 3 months, 6 months, 9 months, 1 year, 2 years, or more, or any timeframe within the recited time limits.

Combination Therapy

In some embodiments, cysteamine and/or cystamine can be administered in combination with other therapies useful for treating fibrosis. Concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

In some embodiments, cysteamine and/or cystamine can be administered in combination (either simultaneously in a single composition or in separate compositions) with corticosteroids (such as prednisone) and/or other medications that suppress the body's immune system, such as cyclophosphamide, azathioprine, methotrexate, penicillamine, and cyclosporine.

In some embodiments, cysteamine and/or cystamine product can be administered in combination (either simultaneously in a single composition or in separate compositions) with inhibitors of the renin-angiotensin system. In some embodiments, cysteamine and/or cystamine product can be administered in combination (either simultaneously in a single composition or in separate compositions) with drugs selected from the group consisting of renin inhibitors, angiotensin II antagonists, and angiotensin converting enzyme (ACE) inhibitors. Examples of renin inhibitors include, but are not limited to, aliskiren and remikiren. Examples of angiotensin II antagonists include, but are not limited to, losartan, irbesartan, olmesartan, candesartan, eprosartan, valsartan, and telmisartan. Examples of ACE inhibitors include, but are not limited to, AB-103, ancovenin, BRL-36378, BW-A575C, CGS-13928C, CL-242817, CV-5975, Equaten, EU-4865, EU-4867, EU-5476, foroxymithine, FPL 66564, FR-900456, Hoe-065, 15B2, indolapril, ketomethylureas, KRI-1177, KRI-1230, L-681176, libenzapril, MCD, MDL-27088, MDL-27467A, moveltipril, MS-41, nicotianamine, pentopril, phenacein, pivopril, rentiapril, RG-5975, RG-6134, RG-6027, RGH-0399, ROO-911, RS-10085-197, RS-2039, RS 5139, RS 86127, RU-44403, S-8308, SA-291, spiraprilat, SQ-26900, SQ-28084, SQ-28370, SQ-28940, SQ-31440, Synecor, utibapril, WF-10129, Wy-44221, Wy-44655, Y-23785, Yissum P-0154, zabicipril, Asahi Brewery AB-47, alatriopril, BMS 182657, Asahi Chemical C-111, Asahi Chemcal C-112, Dainippon DU-1777, mixanpril, Prentyl, zofenoprilat, 1-(-(1-carboxy-6-(4-piperidinyl)hexl)amino)-1-oxopropyl octahydro-1H-indole-2-carboxylic acid, Bioproject BP1.137, Chiesi CHF 1514, Fisons FPL-66564, idrapril, Marion Merrell Dow MDL-100240, perindoprilat, Servier S-5590, alacepril, benazepril, captopril, cilazapril, delapril, enalapril, enalaprilat, fosinopril, fosinoprilat, imidapril, lisinopril, ramipril, perindopril, quinapril, saralasin acetate, temocapril, trandolapril, ceranapril, moexipril, quinaprilat and spirapril.

In some embodiments, cysteamine and/or cystamine product can be administered in combination (either simultaneously in a single composition or in separate compositions) with antioxidants such as glycyrrhizin, schisandra extract, ascorbic acid, glutathione, silymarin, lipoic acid, d-alpha-tocopherol, glycyrrhizin, ascorbic acid, glutathione, and vitamin B-complex. Alternatively, the combination of therapeutics can be administered sequentially.

In some embodiments, cysteamine and/or cystamine product can be administered in combination (either simultaneously in a single composition or in separate compositions) with TGF-β antagonists. The term "TGF-β antagonist" and its cognates such as "inhibitor," "neutralizing," and "downregulating" refer to a compound (or its property as appropriate), or other molecule, which acts as an antagonist of the biological activity of TGF-β. A TGF-β antagonist may, for example, bind to and neutralize the activity of TGF-β; decrease TGF-β expression levels; affect the stability or conversion of the precursor molecule to the active, mature form; interfere with the binding of TGF-β to one or more receptors; or it may interfere with intracellular signaling of a TGF-β receptor. The term "direct TGF-β antagonist" generally refers to any compound that directly downregulates the biological activity of TGF-β. A molecule "directly downregulates" the biological activity of TGF-β if it downregulates the activity by interacting with a TGF-β gene, a TGF-β transcript, a TGF-β ligand, or a TGF-β receptor. Examples of TGF-β antagonists that may be used include but are not limited to monoclonal and polyclonal antibodies directed against one or more isoforms of TGF-β (U.S. Pat. No. 5,571,714; WO 97/13844; and WO 00/66631; WO 05/097832; WO 05/101149; WO 06/086469); dominant negative and soluble TGF-β receptors or antibodies directed against TGF-β receptors (Flavell et al., Nat. Rev. Immunol. 2:46-53 (2002); U.S. Pat. No. 5,693,607; U.S. Pat. No. 6,001,969; U.S. Pat. No. 6,008,011; U.S. Pat. No. 6,010,872; WO 92/00330; WO 93/09228; WO 95/10610; and WO 98/48024; LAP (WO 91/08291); LAP-associated TGF-β (WO 94/09812); TGF-β-binding glycoproteins/proteoglycans such as fetuin (U.S. Pat. No. 5,821,227); decorin, betaglycan, fibromodulin, lumican, and endoglin (U.S. Pat. No. 5,583,103; U.S. Pat. No. 5,654,270; U.S. Pat. No. 5,705,609; U.S. Pat. No. 5,726,149; U.S. Pat. No. 5,824,655; U.S. Pat. No. 5,830,847; U.S. Pat. No. 6,015,693; WO 91/04748; WO 91/10727; WO 93/09800; and WO 94/10187); mannose-6-phosphate or mannose-1-phosphate (U.S. Pat. No. 5,520,926); prolactin (WO 97/40848); insulin-like growth factor 11 (WO 98/17304); extracts of plants, fungi, and bacteria (EU 813875; JP 8119984; and U.S. Pat. No. 5,693,610); antisense oligonucleotides (U.S. Pat. No. 5,683,988; U.S. Pat. No. 5,772,995; U.S. Pat. No. 5,821,234; U.S. Pat. No. 5,869,462; and WO 94/25588); and any mutants, fragments, or derivatives of the above-identified molecules that retain the ability to inhibit the biological activity of TGF-β. Numerous small molecule TGF-β antagonists that may be useful are also well known to those of skill in the art, including, but not limited to, those described in WO 02/62753; WO 02/62776; WO 02/62787; WO 02/62793; WO 02/62794; WO 02/66462; WO 02/94833; WO 03/87304; WO 03/97615; WO 03/97639; WO 04/10929; WO 04/21989; WO 04/22054; WO 04/24159; WO 04/26302; WO 04/26871; U.S. Pat. No. 6,184,226; WO 04/16606; WO 04/47818; WO 04/48381; WO 04/48382; WO 04/48930; WO 04/50659; WO 04/56352; WO 04/72033; WO 04/87056 WO 05/10049; WO 05/032481; WO 05/065691; WO 05/92894; WO 06/026305; WO 06/026306; and WO 06/052568.

In some embodiments, cysteamine and/or cystamine product can be administered in combination (either simultaneously in a single composition or in separate compositions) with tumor necrosis factor (TNF)-α antagonists. The term "TNF-α antagonist" and its cognates such as "inhibitor," "neutralizing," and "downregulating" refer to a compound (or its property as appropriate), or other molecule, which acts as an antagonist of the biological activity of TNF-α. A TNF-α antagonist may, for example, bind to and neutralize the activity of TNF-α; decrease TNF-α expression levels; interfere with the binding of TNF-α to one or more receptors; or it may interfere with intracellular signaling of a TNF-α receptor. The term "direct TNF-α antagonist" generally refers to any compound that directly downregulates the biological activity of TNF-α. A molecule "directly downregulates" the biological activity of TNF-α if it downregulates the activity by interacting with a TNF-α gene, a TNF-α transcript, a TNF-α ligand, or a TNF-α receptor. Examples of TNF-α antagonists include, but not limited to, a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-11), nerelimonmab, infliximab, etanercept, CDP-571, CDP-870, afelimomab, lenercept, and the like.

It is further contemplated that the cysteamine and/or cystamine composition is administered with a second agent useful for treating kidney fibrosis. A second agent may be other therapeutic agents, such as anti-diabetic agents, cytokines, growth factors, other anti-inflammatory agents, anti-coagulant agents, agents that will lower or reduce blood pressure, agents that will reduce cholesterol, triglycerides, LDL, VLDL, or lipoprotein(a) or increase HDL, agents that will increase or decrease levels of cholesterol-regulating proteins, anti-neoplastic drugs or molecules.

Exemplary second agents include, but are not limited to, agents used to treat diabetes, cyclophosphamide, either alone or in combination with mycophenolate mofetil (MMF) or prednisolone, or other corticosteroids, anti-inflammatory agents, azathioprine, IFN-gamma.

Exemplary anti-diabetic agents include, but are not limited to, 1) sulfonylureas (e.g., glimepiride, glisentide, sulfonylurea, AY31637); 2) biguanides (e.g., metformin); 3) alpha-glucosidase inhibitors (e.g., acarbose, miglitol); 4) thiazol-idinediones (e.g., troglitazone, pioglitazone, rosiglitazone, glipizide, balaglitazone, rivoglitazone, netoglitazone, troglitazone, englitazone, AD 5075, T 174, YM 268, R 102380, NC 2100, NIP 223, NIP 221, MK 0767, ciglitazone, adaglitazone, CLX 0921, darglitazone, CP 92768, BM 152054); 5) glucagon-like-peptides (GLP) and GLP analogs or agonists of GLP-1 receptor (e.g., exendin) or stabilizers thereof (e.g., DPP4 inhibitors, such as sitagliptin); and 6) insulin or analogues or mimetics thereof (e.g., LANTUS®).

Additional anti-fibrotic agents contemplated for use in the methods of the present disclosure can be any agent that affects fibrosis. Contemplated agents include, but are not limited to, those that reduce the activity of transforming growth factor-beta (TGF-β) (including but not limited to GC-1008 (Genzyme/MedImmune); lerdelimumab (CAT-152; Trabio, Cambridge Antibody); metelimumab(CAT-192, Cambridge Antibody); LY-2157299 (Eli Lilly); ACU-HTR-028 (Opko Health)) including antibodies that target one or more TGF-β isoforms, inhibitors of TGF-β receptor kinases TGFBR1 (ALK5) and TGFBR2, and modulators of post-receptor signaling pathways; chemokine receptor signaling; endothelin receptor antagonists including inhibitors that target both endothelin receptor A and B and those that selectively target endothelin receptor A (including but not limited to ambrisentan; avosentan; bosentan; clazosentan; darusentan; BQ-153; FR-139317, L-744453; macitentan; PD-145065; PD-156252; PD163610; PS-433540; S-0139; sitaxentan sodium; TBC-3711; zibotentan); agents that reduce the activity of connective tissue growth factor (CTGF) (including but not limited to FG-3019, FibroGen), and also including other CTGF-neutralizing antibodies; matrix metalloproteinase (MMP) inhibitors (including but not limited to MMPI-12, PUP-1 and tigapotide triflutate); agents that reduce the activity of epidermal growth factor receptor (EGFR) including but not limed to erlotinib, gefitinib, BMS-690514, cetuximab, antibodies targeting EGF receptor, inhibitors of EGF receptor kinase, and modulators of post-receptor signaling pathways; agents that reduce the activity of platelet derived growth factor (PDGF) (including but not limited to Imatinib mesylate (Novartis)) and also including PDGF neutralizing antibodies, antibodies targeting PDGF receptor (PDGFR), inhibitors of PDGFR kinase activity, and post-receptor signaling pathways; agents that reduce the activity of vascular endothelial growth factor (VEGF) (including but not limited to axitinib, bevacizumab, BIBF-1120, CDP-791, CT-322, IMC-18F1, PTC-299, and ramucirumab) and also including VEGF-neutralizing antibodies, antibodies targeting the VEGF receptor 1 (VEGFR1, Flt-1) and VEGF receptor 2 (VEGFR2, KDR), the soluble form of VEGFR1 (sFlt) and derivatives thereof which neutralize VEGF, and inhibitors of VEGF receptor kinase activity; inhibitors of multiple receptor kinases such as BIBF-1120 which inhibits receptor kinases for vascular endothelial growth factor, fibroblast growth factor, and platelet derived growth factor; agents that interfere with integrin function (including but not limited to STX-100 and IMGN-388) and also including integrin targeted antibodies; agents that interfere with the pro-fibrotic activities of IL-4 (including but not limited to AER-001, AMG-317, APG-201, and sIL-4Rα) and IL-13 (including but not limited to AER-001, AMG-317, anrukinzumab, CAT-354, cintredekin besudotox, MK-6105, QAX-576, SB-313, SL-102, and TNX-650) and also including neutralizing anti-bodies to either cytokine, antibodies that target IL-4 receptor or IL-13 receptor, the soluble form of IL-4 receptor or derivatives thereof that is reported to bind and neutralize both IL-4 and IL-13, chimeric proteins including all or part of IL-13 and a toxin particularly *pseudomonas* endotoxin, signaling though the JAK-STAT kinase pathway; agents that interfere with epithelial mesenchymal transition including inhibitors of mTor (including but not limited to AP-23573); agents that reduce levels of copper such as tetrathiomolybdate; agents that reduce oxidative stress including N-acetyl cysteine and tetrathiomolybdate; and interferon gamma. Also contemplated are agents that are inhibitors of phosphodiesterase 4 (PDE4) (including but not limited to Roflumilast); inhibitors of phosphodiesterase 5 (PDE5) (including but not limited to mirodenafil, PF-4480682, sildenafil citrate, SLx-2101, tadalafil, udenafil, UK-369003, vardenafil, and zaprinast); or modifiers of the arachidonic acid pathway including cyclooxygenase and 5-lipoxegenase inhibitors (including but not limited to Zileuton). Further contemplated are compounds that reduce tissue remodeling or fibrosis including prolyl hydrolase inhibitors (including but not limited to 1016548, CG-0089, FG-2216, FG-4497, FG-5615, FG-6513, fibrostatin A (Takeda), lufironil, P-1894B, and safironil) and peroxisome proliferator-activated receptor (PPAR)-gamma agonists. (including but not limited to pioglitazone and rosiglitazone).

Other specific anti-fibrotic agents contemplated include relaxin, pirfenidone, ufironil, surifonil, a TGF-β antibody, CAT-192, CAT-158; ambresentan, thelin; FG-3019, a CTGF antibody; anti-EGFR antibody; a EGFR kinase inhibitor; tarceva; gefitinib; PDGF antibody, PDGFR kinase inhibitor; gleevec; BIBF-1120, VEGF, FGF, and PDGF receptor inhibitor; anti-integrin antibody; IL-4 antibody; tetrathiomolybdate, a copper chelating agent; interferon-gamma; NAC, a cysteine pro-drug; hepatocyte growth factor (HGF); KGF; angiotension receptor blockers, ACE inhibitors, rennin inhibitors; COX and LO inhibitors; Zileuton; monteleukast; avastin; statins; PDE5 inhibitors, such as sildenafil, udenafil, tadalafil, vardenafil, or zaprinast; rofumilast; etanercept (Enbrel); procoagulant; prostaglandins, such as PGE2, PRX-08066, a 5HT2B receptor antagonist; cintredekin besudotox, a chimeric human IL13 conjugated to a genetically engineered *Pseudomonas* exotoxin; roflumilast, a PDE4 inhibitor; FG-3019, an anti-connective tissue growth factor human monoclonal antibody; GC-1008, a TGF-β human monoclonal antibody; treprostinil, a prostacyclin analog; interferon-α; QAX-576, a IL13 modulator; WEB 2086, a PAF-receptor antagonist; imatinib mesylate; FG-1019; Suramin; Bosentan; IFN-1b; anti-IL-4; anti-IL-13; taurine, niacin, NF-κB antisense oligonucleotides; and nitric oxide synthase inhibitors.

It is contemplated the cysteamine composition and the second agent may be given simultaneously, in the same formulation. It is further contemplated that the agents are administered in a separate formulation and administered concurrently, with concurrently referring to agents given within 30 minutes of each other.

In another aspect, the second agent is administered prior to administration of the cysteamine and/or cystamine. Prior administration refers to administration of the second agent within the range of one week prior to treatment with cysteamine, up to 30 minutes before administration of cysteamine. It is further contemplated that the second agent is administered subsequent to administration of the cysteamine and/or cystamine composition. Subsequent administration is meant to describe administration from 30 minutes after cysteamine and/or cystamine treatment up to one week after cysteamine and/or cystamine administration.

It is further contemplated that other adjunct therapies may be administered, where appropriate. For example, the patient may also be administered a diabetic diet or food plan, surgical therapy, or radiation therapy where appropriate.

Formulation and Delivery

The cysteamine and/or cystamine product of the present embodiments may be formulated into compositions together with pharmaceutically acceptable carriers for parenteral injection, for oral administration in solid or liquid form, for rectal administration, and the like. The cysteamine and/or cystamine product may be administered orally (including buccal, sublingual, inhalation), nasally, rectally, vaginally, intravenously, intradermally, subcutaneously and topically. Cysteamine and/or cystamine product may be formulated into compositions suitable for administration for example with suitable carriers, diluents, thickeners, adjuvants, etc., as are routine in the formulation art. Compositions of the present embodiments may also include additional active ingredients. Dosage forms include solutions, powders, tablets, capsules, gel capsules, suppositories, topical ointments and creams and aerosols for inhalation.

In one embodiment, administration is performed at the site of affected tissue needing treatment by direct injection into the site or via a sustained delivery or sustained release mechanism, which can deliver the formulation internally. For example, biodegradable microspheres or capsules or other biodegradable polymer configurations capable of sustained delivery of a composition (e.g., a soluble polypeptide, antibody, or small molecule) can be included in the formulations of the invention implanted at the site.

In some embodiments, cysteamine and/or cystamine product is administered via oral delivery. Compositions for oral administration include powders or granules, suspensions or solutions in water or non-aqueous media, oil-in-water emulsions or water-in-oil liquid emulsions, capsules, sachets, troches, tablets or SECs (soft elastic capsules or caplets). Thickeners, flavoring agents, diluents, emulsifiers, dispersing aids, carrier substances of binders may be desirably added to such formulations. The use of such formulations has the effect of delivering the cysteamine and/or cystamine to the alimentary canal for exposure to the mucosa thereof. Accordingly, the formulation can consist of material effective in protecting the product from pH extremes of the stomach, or in releasing the product over time, to optimize the delivery thereof to a particular mucosal site. A tablet may be made by compression or molding, optionally with one or more accessory ingredients. The tablets may optionally be coated or scored and may be formulated so as to provide slow or controlled release of the active ingredients therein.

Compositions may be formulated in a conventional manner using additional pharmaceutically acceptable carriers or excipients as appropriate. Thus, the composition may be prepared by conventional means with additional carriers or excipients such as binding agents (e.g., pregelatinised maize starch, polyvinylpyrrolidone or hydroxypropyl methylcellulose); filters (e.g., lactose, microcrystalline cellulose or calcium hydrogen phosphate); lubricants (e.g., magnesium stearate, talc or silica); disintegrates (e.g., starch or sodium starch glycolate); or wetting agents (e.g., sodium lauryl sulfate). Tablets may be coated by methods well known in the art. The preparations may be also contain flavoring, coloring and/or sweetening agents as appropriate.

Pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided soled carriers or both, and then, if necessary, shaping the product.

Delayed or Controlled Release Dosage Forms

In some embodiments, the cysteamine and/or cystamine product is a delayed or controlled release dosage form. The preparation of delayed, controlled or sustained/extended release forms of pharmaceutical compositions with the desired pharmacokinetic characteristics is known in the art and can be accomplished by a variety of methods. For example, oral controlled delivery systems include dissolution-controlled release (e.g., encapsulation dissolution control or matrix dissolution control), diffusion-controlled release (reservoir devices or matrix devices), ion exchange resins, osmotic controlled release or gastroretentive systems. Dissolution controlled release can be obtained, e.g., by slowing the dissolution rate of a drug in the gastrointestinal tract, incorporating the drug in an in soluble polymer, and coating drug particles or granules with polymeric materials of varying thickness. Diffusion controlled release can be obtained, e.g., by controlling diffusion through a polymeric membrane or a polymeric matrix. Osmotically controlled release can be obtained, e.g., by controlling solvent influx across a semipermeable membrane, which in turn carries the drug outside through a laser-drilled orifice. The osmotic and hydrostatic pressure differences on either side of the membrane govern fluid transport. Prolonged gastric retention may be achieved by, e.g., altering density of the formulations, bioadhesion to the stomach lining, or increasing floating time in the stomach. For further detail, see the Handbook of Pharmaceutical Controlled Release Technology, Wise, ed., Marcel Dekker, Inc., New York, N.Y. (2000), incorporated by reference herein in its entirety, e.g., Chapter 22 ("An Overview of Controlled Release Systems").

The concentration of cysteamine and/or cystamine product in these formulations can vary widely, for example from less than about 0.5%, usually at or at least about 1% to as much as 15 or 20% by weight and are selected primarily based on fluid volumes, manufacturing characteristics, viscosities, etc., in accordance with the particular mode of administration selected. Actual methods for preparing administrable compositions are known or apparent to those skilled in the art and are described in more detail in, for example, Remington's Pharmaceutical Science, 15th ed., Mack Publishing Company, Easton, Pa. (1980).

In certain embodiments, the delayed or controlled release form is enterically coated. An enterically coated drug or tablet refers, generally, to a drug or tablet that is coated with a substance (an "enteric coating") that remains intact or substantially intact such that the drug or tablet is passed through the stomach but dissolves and releases the drug in the small intestine. Enterically coated cysteamine products are described in International Patent Publication Nos. WO 07/089670 and WO 09/070781, hereby incorporated by reference in their entirety.

Briefly, an enteric coating can be a polymer material or materials which encase a medicament core (e.g., cysteamine, cysteamine, CYSTAGON™ or other cysteamine and/or cystamine product). Typically a substantial amount or all of the enteric coating material is dissolved before the medicament or therapeutically active agent is released from the dosage form, so as to achieve delayed dissolution or delivery of the medicament core. A suitable pH-sensitive polymer is one which will dissolve in intestinal environment at a higher pH level (pH greater than 4.5), such as within the small intestine, and therefore permit release of the pharmacologically active substance in the regions of the small intestine and not in the upper portion of the GI tract, such as the stomach. Enteric coatings for acid-resistant tablets, capsules and caplets include, but are not limited to, acetate phthalate, propylene glycol and sorbitan monoleate.

For administration of the dosage form, e.g., a tablet or capsule or other oral dosage form comprising the enterically coated cysteamine and/or cystamine product, a total weight in the range of approximately 100 mg to 1000 mg is used. In exemplary embodiments, the dosage form is orally administered to a patient suffering from kidney disease. Administration may continue for at least 3 weeks, 4 weeks, 6 weeks, 8 weeks, 3 months, 6 months, 9 months, 1 year, 2 years, or more, or any timeframe within the recited time limits.

The following Examples are presented for the purposes of illustration and should not be construed as limitations.

Example 1

IP Cysteamine HCL Dose Trial

Figure 4:
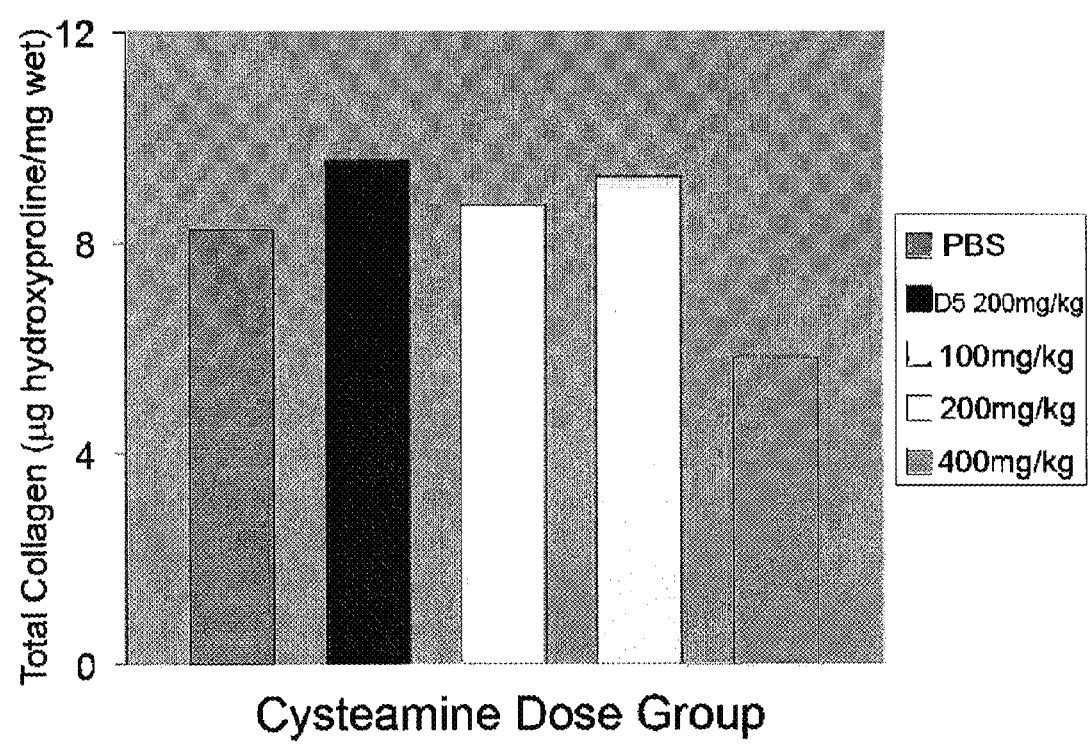
FIG. 4 shows a graph depicting total kidney collagen as measured by hydroxyproline concentration at day 14 after UUO in groups of mice (n=2/group) receiving intraperitoneal injections of PBS (control), 100 mg/kg cysteamine HCL, 200 mg/kg cysteamine HCL or 400 mg/kg cysteamine HCL.

Unilateral ureteral obstruction (UUO) was performed on ten mice. Starting on the day of UUO, two of the mice were given daily intraperitoneal (IP) injections of phosphate buffered saline (PBS), two of the mice were given daily intraperitoneal (IP) injections of 100 mg/kg freshly mixed cysteamine HCL in PBS, and two of the mice were given daily intraperitoneal (IP) injections of 200 mg/kg freshly mixed cysteamine HCL in PBS. One group of mice (n=2) was given daily intraperitoneal (IP) injections of freshly mixed cysteamine HCL in PBS starting at a dose of 200 mg/kg on the day of UUO and the dose was gradually increased every two days to a maximum dose of 400 mg/kg. Another group of mice (n=2) was given daily intraperitoneal (IP) injections of 200 mg/kg freshly mixed cysteamine HCL in PBS starting 5 days after UUO (D5 200 mg/kg). Possible seizures and somnolence were observed in mice given cysteamine HCL immediately after surgery and several mice died at high dose levels. Surviving mice were sacrificed at day 14 after UUO and total renal collagen levels (μg hydroxyproline/mg) were measured. The results of the IP cysteamine HCL dose trials are shown in FIG. 4. At day 14, the 400 mg/kg dose group exhibited decreased total collagen levels compared to placebo (PBS).

Example 2

Oral Cystagon® Dose Trial

UUO was performed on sixteen mice and placebo (n=4 mice) or 200 mg/kg cysteamine bitartrate dissolved in drinking water administered on the first day after UUO. It was assumed that an average 25 g mouse drinks 5 mLs of water per day; cysteamine bitartrate was diluted in water and prepared daily to provide 200 mg/kg, 400 mg/kg or 600 mg/kg. One group of mice (n=4) received 200 mg/kg cysteamine bitartrate dissolved in drinking water for fourteen days. In one group of mice (n=4), the dose of cysteamine bitartrate dissolved in the drinking water was increased every 2 days to a maximum of 400 mg/kg. In one group of mice (n=4), the dose of cysteamine bitartrate dissolved in the drinking water was increased every 2 days to a maximum of 600 mg/kg. No deaths or abnormal behavior was observed, even at high doses. Mice were sacrificed at day 14 after UUO and total renal collagen levels (μg hydroxyproline/mg) were measured. Total collagen in the tissue was calculated on the assumption that collagen contains 12.7% hydroxyproline by weight. As shown in FIG. 5, the severity of fibrosis as measured by total collagen content was attenuated in mice receiving 400 mg/kg and 600 mg/kg cysteamine bitartrate dissolved in drinking water.

Example 3

Cysteamine Treatment Reduces Severity of Fibrosis in UUO Kidneys

Unilateral ureteral obstruction (UUO) was performed on 8 week-old wild-type male mice on a C57BL6 background. The degree of renal fibrosis was investigated using two doses of cysteamine bitartrate: 400 and 600 mg/kg/day. Cysteamine bitartrate was added to drinking water that was freshly made every 24 h starting on the first day after UUO at 200 mg/kg and the dose was increased every 2 days until the maximum dosage was reached. It was assumed that an average 25 g mouse drinks 5 mLs of water per day; cysteamine bitartrate was diluted in water and prepared daily to provide 400 mg/kg or 600 mg/kg. The control group did not receive cysteamine bitartrate treatment. Groups of mice (n=8-10 mice per group at each time-point) were studied 3, 7, 14, and 21 days after the onset of chronic injury induced by UUO.

Total collagen was measured as hydroxyproline concentration in hydrolysates extracted from frozen normal (unobstructed) and UUO kidney samples. Total collagen in the tissue was calculated on the assumption that collagen contains 12.7% hydroxyproline by weight. Both doses, 400 and 600 mg/kg/day, showed statistically significant reductions (P<0.01) in kidney collagen levels by day 14. Compared to the untreated group, mice receiving 600 mg/kg/day cysteamine bitartrate showed a 21 percent decrease in collagen levels by day 14 and a 25 percent decrease in collagen levels at day 21 after UUO (FIG. 6). Collagen reduction was confirmed by sirius red staining Example 4

Cysteamine Decreases ECM Gene Transcription in UUO Kidneys in a Dose Dependent Manner One mechanism by which cysteamine treatment is believed to slow or halt fibrosis is through reduction of ECM synthesis rates.

Unilateral ureteral obstruction (UUO) was performed on 8 week-old wild-type male mice on a C57BL6 background. Cysteamine bitartrate was added to the drinking water daily starting on the first day after UUO at 200 mg/kg and the dose was increased every 2 days to a maximum dose of either 400 mg/kg (n=6-8 mice) or 600 mg/kg (n=6-8 mice). It was assumed that an average 25 g mouse drinks 5 mLs of water per day; cysteamine bitartrate was diluted in water and prepared daily to provide 400 mg/kg or 600 mg/kg. The control group did not receive cysteamine bitartrate treatment. The kidneys were harvested at 3, 7, and 14 days after UUO.

Extracellular matrix (ECM) gene mRNA levels were measured by semiquantitative real-time PCR (qPCR) in both doses at 3, 7 and 14 days after UUO. Real-time qPCR) was performed with specific primers for collagen 1A1, collagen 3A1, fibronectin, and other profibrotic and proinflammatory genes using standard protocols. Semi-quantitative real-time qPCR data was analyzed with REST software using both GAPDH and 18S as reference genes. Reactions were run in triplicate, and mean threshold crossing cycle (Ct) values were compared. ‡$P<0.05$; †$P<0.01$.

ECM gene transcription levels were significantly down-regulated in UUO kidneys of cysteamine-treated mice. Procollagen I mRNA levels were 56 percent lower in the mice treated with 600 mg/kg at day 14. At day 7 after UUO, despite no difference in total collagen (See Example 3 and FIG. 6), there was a nearly 40 percent reduction in kidney fibronectin and procollagen III mRNA levels in mice treated with 400 mg/kg/day cysteamine bitartrate and a nearly 60 percent reduction in fibronectin, procollagen I and procollagen III at higher doses of cysteamine bitartrate (600 mg/kg/day). Results are summarized in FIGS. 7A and 7B.

Example 5

Cysteamine Decreases Myofibroblast Activation and Accumulation

Myofibroblast activation and accumulation was examined after UUO by measuring the expression of α-smooth muscle actin (α-SMA), a marker of myofibroblast activation. Interstitial myofibroblasts are the primary matrix-producing cell in response to kidney injury.

UUO was performed on 8 week-old wild-type male mice on a C57BL6 background. Cysteamine bitartrate was added to the drinking water daily starting on the first day after UUO at 200 mg/kg and the dose was increased every 2 days to a maximum dose of either 400 mg/kg (n=6-8 mice) or 600 mg/kg (n=6-8 mice). It was assumed that an average 25 g mouse drinks 5 mLs of water per day; cysteamine bitartrate was diluted in water and prepared daily to provide 400 mg/kg or 600 mg/kg. The control group did not receive cysteamine bitartrate treatment. Animals were injected with 50 mg/kg of BrdU at 10 mg/mL the day prior to sacrifice. Kidneys were harvested at days 7 and 14 after UUO. Cell proliferation was measured by counting BrdU positive cells using a monoclonal anti-BrdU antibody. Myofibroblast recruitment was quantified after immunoperoxidase staining using peroxidase-conjugated murine anti-human α-smooth muscle actin (α-SMA) 1A4 monoclonal antibody (Sigma).

Statistically significant reductions in the numbers of α-SMA-positive myofibroblasts were observed for both doses of cysteamine at day 7 and day 14 after UUO ($P<0.01$). The largest reductions of 38% and 47% were seen at day 7 in the 400 mg/kg and 600 mg/kg groups, respectively. At day 14, the 400 mg/kg dosage group exhibited a 24% reduction in α-SMA-positive myofibroblasts and the 600 mg/kg dosage group exhibited a 33% reduction in α-SMA-positive myofibroblasts. See FIG. 8A to 8D.

Example 6

Cysteamine Blocks Interstitial Macrophage Infiltration at Advanced Time Points

UUO was performed on 8 week-old wild-type male mice on a C57BL6 background. Cysteamine bitartrate was added to the drinking water daily starting at a dose of 200 mg/kg on the first day after UUO and dose was increased every 2 days to a maximum dose of either 400 mg/kg (n=4-8 mice) or 600 mg/kg (n=5-8 mice). It was assumed that an average 25 g mouse drinks 5 mLs of water per day; cysteamine bitartrate was diluted in water and prepared daily to provide 400 mg/kg or 600 mg/kg. The control group (n=5-8 mice) did not receive cysteamine bitartrate treatment. The kidneys (obstructed and contralateral) were harvested at day l and day 14 after UUO. Macrophage accumulation was analyzed by confocal staining using F4/80 rat anti-mouse macrophage monoclonal antibody (Serotec Ltd., Oxford, UK).

Computed-assisted image analysis of immunohistochemically stained kidney sections at day 14 UUO show significantly less interstitial inflammation as measured by the number of F4/80+ interstitial macrophages and significantly fewer interstitial myofibroblasts. FIG. 9A to 9D shows representative confocal images (400×) of F4/80-positive interstitial macrophages and a graph summarizing the results of semi-quantitative analysis of F4/80-positive interstitial area. (n=4-8/group; †$P<0.01$). A significant reduction (34%) in interstitial macrophage infiltration was observed at day 14 in mice treated with 600 mg/kg/day. No difference in interstitial macrophage infiltration was seen at day 7.

Example 7

Cysteamine Bitartrate Modulates Profibrotic Signaling at Advanced Timepoints

The expression patterns of pro-inflammatory and pro-fibrotic cytokines were investigated at day 7 and day 14 in total kidney homogenate by semi-quantitative real time qPCR.

UUO was performed on 8 week-old wild-type male mice on a C57BL6 background. Cysteamine bitartrate was added to the drinking water daily starting at a dose of 200 mg/kg on the first day after UUO and the dose was increased every 2 days to a maximum dose of either 400 mg/kg (n=6-8 mice) or 600 mg/kg (n=6-8 mice). It was assumed that an average 25 g mouse drinks 5 mLs of water per day; cysteamine bitartrate was diluted in water and prepared daily to provide 400 mg/kg or 600 mg/kg. The control group (n=5-8 mice) did not receive cysteamine bitartrate treatment. The kidneys (obstructed and contralateral) were harvested at day l and day 14 after UUO.

Semi-quantitative real-time PCR was performed with specific primers to TGF-β and TGF-β receptor 1 genes using iCycler (Bio-Rad) with standard protocol. Relative mRNA transcription levels of TGF-β and TGF-β receptor 1 genes in UUO kidneys of cysteamine treated mice were determined with respect to control mice. Semi-quantitative real-time PCR data was analyzed with REST software using both GAPDH and 18S as reference genes. Each sample was performed in triplicate. (‡$P<0.05$, †$P<0.01$).

At day 7 after UUO, expression of both the profibrotic cytokine TGF-β and the TGF-β receptor were significantly up-regulated by approximately 60 percent in mice treated with high doses of cysteamine bitartrate compared to control mice ($P<0.01$). This suggests that the down-regulation of ECM gene transcription observed at day 7 is TGF-β independent. At day 14, however, the mRNA levels of TGF-β and the TGF-β receptor were significantly down-regulated by 47 percent and 64 percent in mice treated with 400 mg/kg or 600 mg/kg cysteamine bitartrate, respectively, compared to control mice (P<0.05). No difference was observed in the expression levels of IL-1β, TNF-α, IL-6, Gal-3, and Endo180 at day 14. See Table 2 and FIGS. 10A and 10B.

TABLE 2

Expression of TGF-β and the TGF-β receptor
After UUO in Cysteamine Treated Mice

|  | Cystagon 400 mg/kg Day 7 | Cystagon 600 mg/kg Day 7 | Cystagon 400 mg/kg Day 14 | Cystagon 600 mg/kg Day 14 |
|---|---|---|---|---|
| TGF-β | 0.52 ± 0.13 | 0.74 ± 0.19** | 0.61 ± 0.21 | 0.66 ± 0.22 |
| TGF-β receptor | 0.72 ± 0.30 | 1.38 ± 0.36** | 0.56 ± 0.22 | 0.42 ± 0.13** |

Example 8

Cysteamine Modulates Antioxidant Status at Early Timepoints

In order to investigate the importance of total redox status during fibrotic injury, total kidney thiol content was measured as an indicator of antioxidant status.

UUO was performed on 8 week-old wild-type male mice on a C57BL6 background (n=5/group). Cysteamine bitartrate was added to the drinking water daily starting at a dose of 200 mg/kg on the first day after UUO and the dose was increased every 2 days to a maximum dose of either 400 mg/kg or 600 mg/kg. It was assumed that an average 25 g mouse drinks 5 mLs of water per day; cysteamine bitartrate was diluted in water and prepared daily to provide 400 mg/kg or 600 mg/kg. The control group did not receive cysteamine bitartrate treatment. The kidneys (obstructed and contralateral) were harvested at days 7, 14 and 21 after UUO. Tissue from contralateral and UUO kidneys was processed in antioxidant buffer and analyzed for total thiol content fluorometrically and normalized to protein content using a Measure-iT™ Thiol Assay Kit (Invitrogen).

Figure 11:
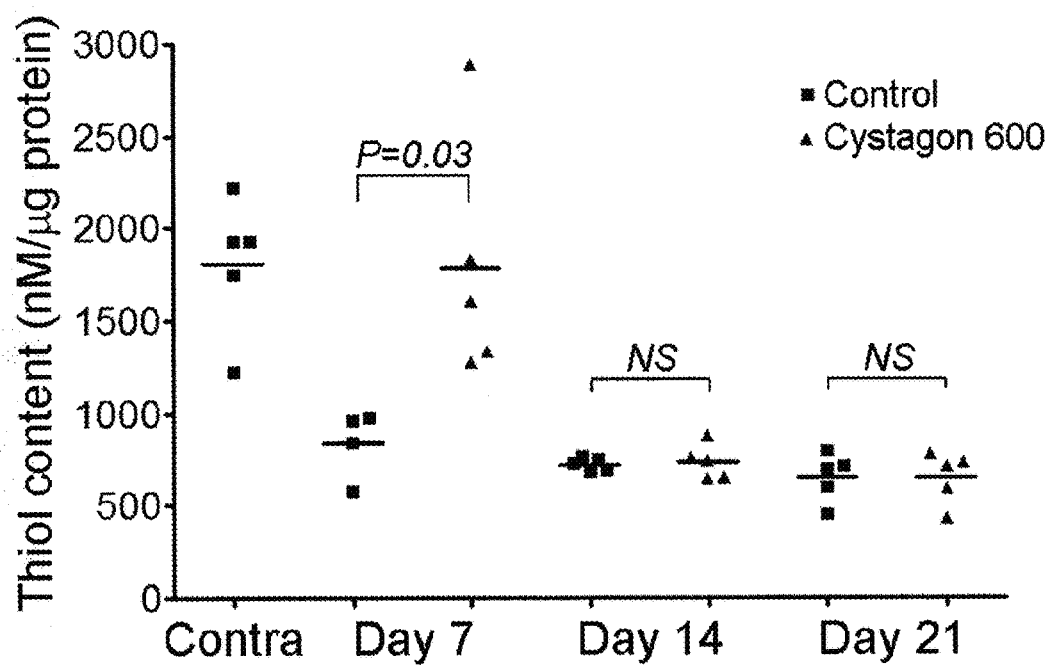
FIG. 11 shows a graph depicting thiol content (nM/μg protein) of tissue from contralateral and UUO kidneys harvested at days 7, 14, and 21 from mice administered placebo or 600 mg/kg cysteamine bitartrate.

Total kidney thiol content in UUO tissue was significantly decreased 40 percent compared to the contralateral kidney in control dose mice (contralateral vs. UUO, n=5-6/group: 1397 vs. 838 mM thiol, P<0.01). At day 7 after UUO, total kidney thiol content remained at levels close to that of the contralateral kidney in the 400 mg/kg or 600 mg/kg cysteamine-treated mice compared to control (FIG. 11). In addition, there was no difference between cysteamine-treated and control mice in the modulation of the expression of the oxidant and anti-oxidant genes Nox2, Nox4, and SOD1 as determined by semi-quantitative real time qPCR at day 7 and day 14 (data not shown).

Example 9

Evaluation of the Role of Endogenous Cysteamine Synthesized by an Enzamatic Pathway Encoded by the Vanin-1 Gene The role of endogenous cysteamine synthesized via an enzymatic pathway that is encoded by the vanin gene in protection against fibrosis was examined by comparing the degree of fibrosis between littermate controls (Vanin+/+) and Vanin−/− mice. UUO was performed on 8 week-old Vanin+/+ (n=3-7) and Vanin−/− (n=3-6) mice. The kidneys (obstructed and contralateral (NK)) were harvested at days 14 and 21 after UUO and total renal collagen levels (μg hydroxyproline/mg) were measured. See FIG. 12B.

No statistically significant difference in total collagen levels was observed in the UUO kidneys of Vanin+/+ and Vanin−/− at 14 days after UUO. There was, however, a non-significant trend toward more fibrosis in the Vnn1−/− UUO kidneys at advanced stages (day 21 after UUO). The Vanin−/− strain used for these studies was not in a pure C57BL/6 background and the values for total collagen were much lower than typically seen in C57BL/6 mice. Back-crossing of the Vanin−/− mutation into a pure C57BL/6 background will be performed to determine if the observed differences can be accentuated.

In order to test whether the rate of progression of the renal phenotype in Cystinosin deficient (Ctns−/−) mice is attenuated by the endogenous cysteamine synthesized via a vanin-1 mediated enzymatic pathway, a colony of Ctns−/− Vanin-1−/− double knock-out mice was generated. Rates of polyuria significantly increased in Ctns−/− Vanin-1−/− knock-out mice at 6 months of age; however, the difference diminished at 9 months and there was no difference in kidney weight of the double knock-out mice compared to heterozygous controls. There was a significant increase in blood urea nitrogen (BUN) in the double knock-out mice compared to heterozygous controls at 10 months (Heterozygous controls vs. Double knock-out, =8/group: 17.6±1.0 vs. 22.7±1.4 mg/dL, P=0.01). Masson trichrome staining showed an increase in glomerulosclerosis and mild interstitial fibrosis at 12 months in the double knock-out mice compared to heterozygous controls. However, in-depth fibrosis analysis (Total collagen, picrosirius red staining, Masson trichrome, and BUN) of the Ctns/Vnn1 double knock-out mice did not suggest any increase in renal fibrosis with the addition of the Vnn1 gene deletion compared to Ctns−/− mice.

Example 10

Examination of Cystinosin Deficient Interstitial Macrophages

In order to examine the fibrotic response of cystinosin deficient (Ctns−/−) interstitial macrophages (Mφ) in response to renal injury (such as tubular apoptosis), a cohort of Ctns−/− mice on a C57BL/6 background was followed for 12+ months.

Total renal collagen levels (μg hydroxyproline/mg) were measured in the kidneys of Ctns+/+ and Ctns−/− mice at 3 and 12 months of age. Total collagen in the tissue was calculated on the assumption that collagen contains 12.7% hydroxyproline by weight. Macrophage accumulation was analyzed by confocal staining using F4/80 rat anti-mouse macrophage monoclonal antibody (Serotec Ltd., Oxford, UK).

As seen in FIG. 13C total kidney collagen significantly increased 2.3-fold in the kidneys of Ctns−/− mice between 3 and 12 months of age. The increase in total collagen corresponded to an increase in F4/80+ interstitial Mφs over the same time period. See FIGS. 13A and B.

Unilateral ureteral obstruction (UUO) was performed on 3-month old Ctns+/+ and Ctns−/− mice. Kidneys (obstructed and contralateral) were then harvested at day 14 after UUO. Total collagen was measured as hydroxyproline concentration in hydrolysates extracted from frozen normal (contralateral) and UUO kidney samples. Macrophage accumulation in the obstructed and contralateral at day 14 was analyzed by confocal staining using F4/80 rat anti-mouse macrophage monoclonal antibody (Serotec Ltd., Oxford, UK).

Figure 14A:
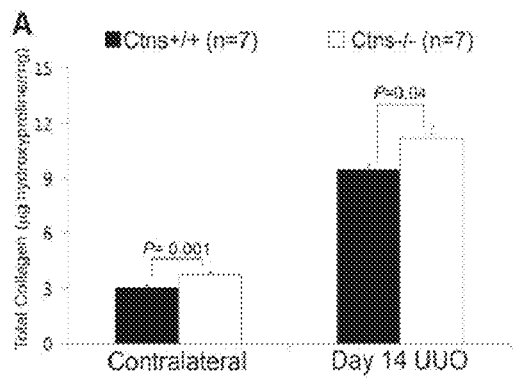
FIG. 14A shows a graph depicting total collagen in kidneys (contralateral and UUO) of Ctns+/+ (n=7) and Ctns−/− (n=7) mice at day 14 after UUO.
Figure 14B:
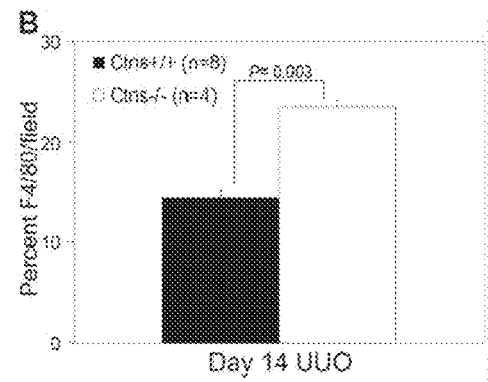
FIG. 14B shows a graph summarizing the quantification of F4/80+macrophages in comparable areas of Ctns+/+ (n=8) and Ctns−/− (n=4) day 14 UUO kidneys.
Figure 14C:
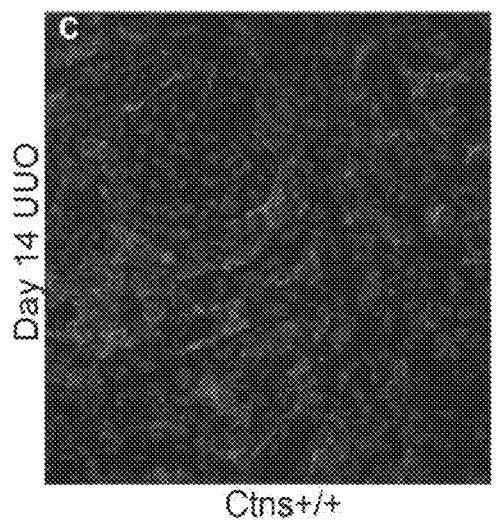
FIG. 14C shows a representative confocal image of F4/80+ interstitial macrophages in a Ctns+/+ day 14 UUO kidney.
Figure 14D:
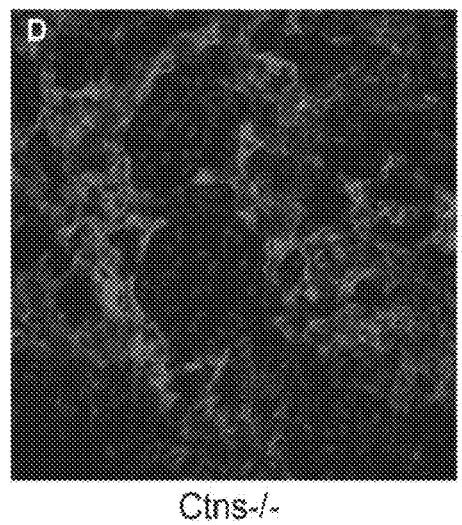
FIG. 14D shows a representative confocal image of F4/80+ interstitial macrophages in a Ctns−/− day 14 UUO kidney.

As seen in FIGS. 14A and 14B, Ctns−/− mice subjected to UUO developed significantly worse fibrosis (19% higher total collagen) with 63% more F4/80+ interstitial Mφs compared to Ctns+/+ mice.

The expression pattern of cystinosin in chronically damaged kidneys was investigated. UUO was performed on 8 week-old Ctns+/+C57BL/6 mice. The kidneys (obstructed and contralateral) were then harvested at days 3, 7 and 14 after UUO and semi-quantitative real-time PCR was performed with specific primers to cystinosin gene using iCycler (Bio-Rad) using a standard protocol. Relative mRNA transcription levels of cystinosin in UUO kidneys was normalized with respect to GAPDH.

Figure 15A:
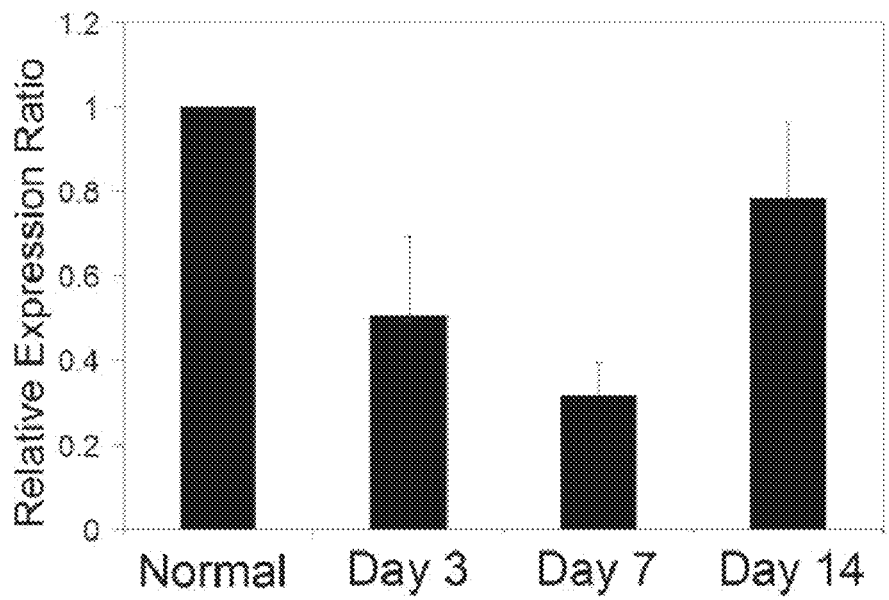
FIG. 15A shows a graph depicting the relative expression ratio of cystinosin (Ctns) in normal (contralateral) kidney and UUO kidneys at days 3, 7 and 14 (n=4/group).

In the UUO model induced in Ctns+/+ C57BL/6 mice, semi-quantitative real-time RT-PCR revealed that Ctns gene expression initially declined (days 3 and 7), likely reflecting tubular injury, and then increased at day 14 (FIG. 15A).

RNA isolated was isolated from Ctns+/+ thioglycollate peritoneal macrophages that were either cultured alone or co-cultured with apoptotic renal tubular cells (+IRR MCT) for 24 hours. Semiquantitative RT-PCR was performed with specific primers to cystinosin gene using iCycler (Bio-Rad) using a standard protocol. Relative mRNA transcription levels of cystinosin in the macrophages was normalized with respect to GAPDH.

Figure 15B:
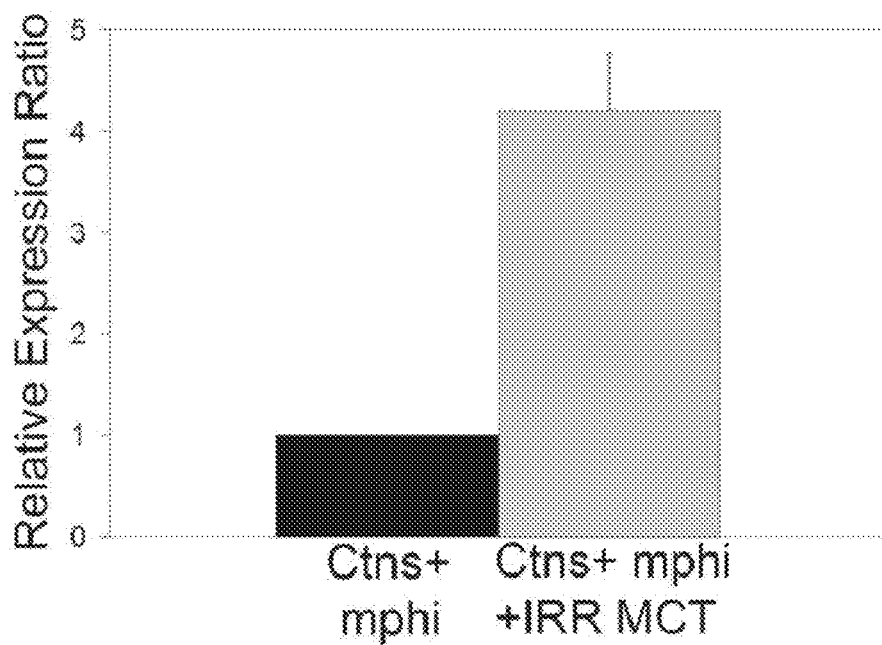
FIG. 15B shows a graph depicting the relative expression ratio of Ctns in thioglycollate peritoneal macrophages (Mphi) and in Mphi co-cultured with apoptotic renal tubular cells (+IRR MCT).

Ctns mRNA expression was confirmed in wild-type peritoneal Mφ and Ctns expression was increased 4-fold in macrophages after phagocytosis of apoptotic proximal tubular cells (FIG. 15B).

Cytokine profiling studies were performed to elucidate differences in macrophage function between Ctns+/+ and Ctns−/− Mφ. An antibody-based method of isolating kidney CD11b+ Mφ by both the AutoMACS® magnetic bead system and by flow cytometry (FACS) was developed and Ctns+/+ and Ctns−/− CD11b+ Mφ were isolated.

An in vitro model to investigate the effects of apoptotic tubular cells on macrophage activation was then developed to study the downstream effects that are triggered by tubular apoptosis following their phagocytic clearance. Thioglycollate peritoneal macrophages were co-cultured with apoptotic mouse cortical tubular cells (MCT) cells for 24 hours in serum free media. Cells were harvested and RNA extracted for semiquantitative real time RT-PCR. Semi-quantitative real-time PCR was performed with specific primers to TNF-α, TNF-α Receptor, TGF-β, and TGF-β Receptor genes using iCycler (Bio-Rad) with a standard protocol. Relative mRNA transcription levels of TNF-α, TNF-α Receptor, TGF-β, and TGF-β Receptor in the macrophages was normalized with respect to GAPDH.

Figure 16A:
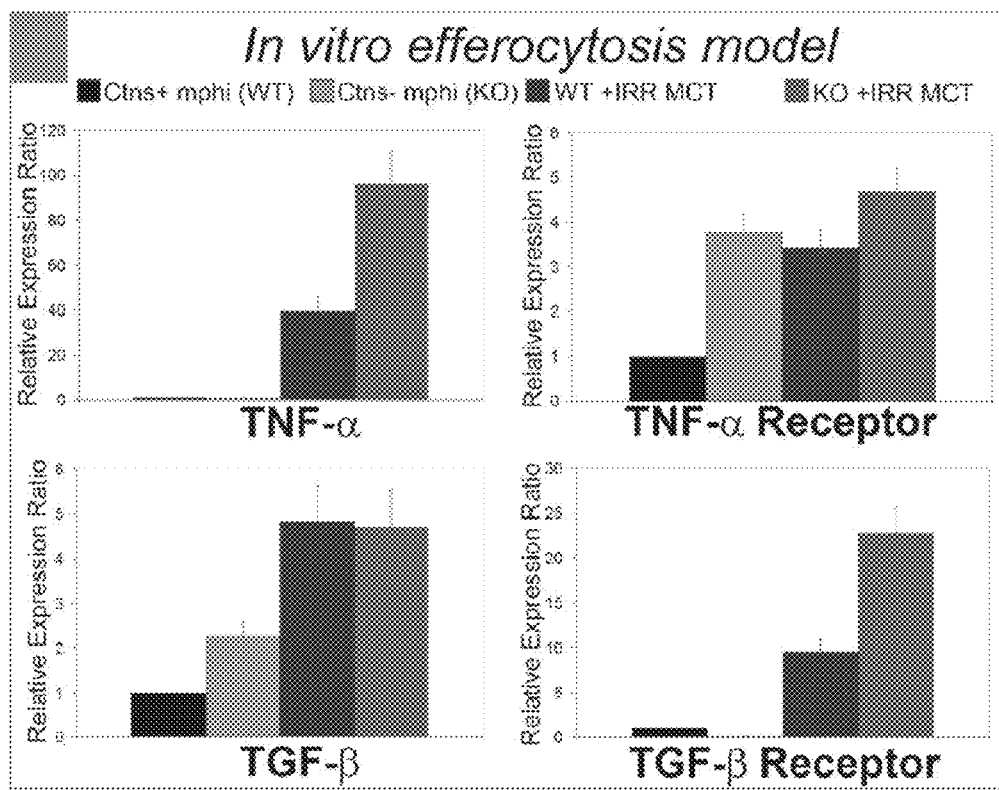
FIG. 16A shows graphs depicting the relative expression ratio of TNF-α, TNF-α Receptor, TGF-β, and TGF-β Receptor in Ctns+/+ and Ctns−/− macrophages and in Ctns+/+ and Ctns−/− macrophages after efferocytosis.
Figure 16B:
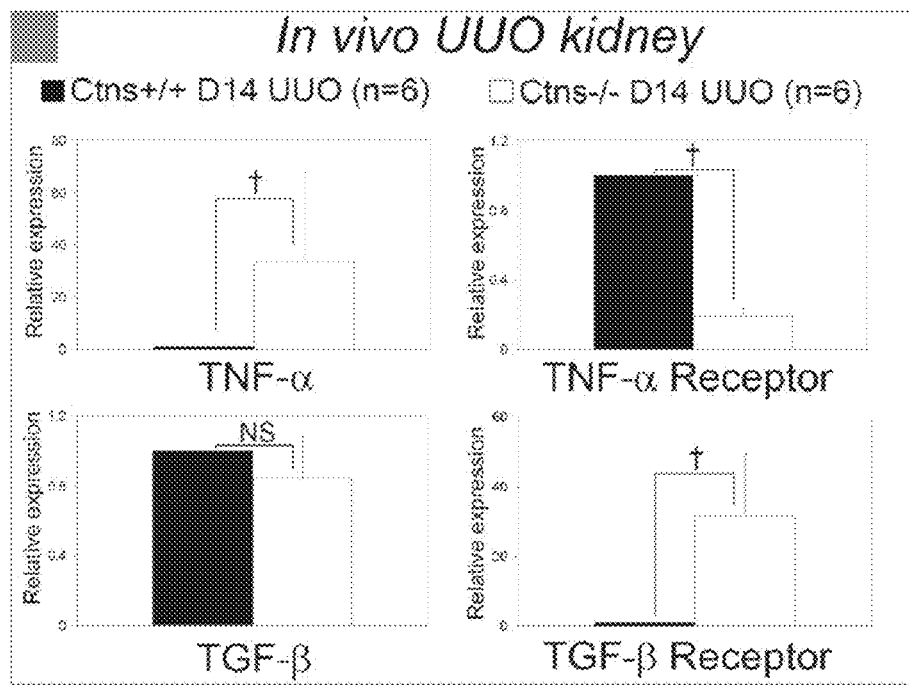
FIG. 16B shows graphs depicting the relative expression levels of TNF-α, TNF-α Receptor, TGF-β, and TGF-β Receptor in Ctns+/+ and Ctns−/− UUO kidneys at day 14. (†P<0.01, NS=not significant, n=6/group.)

The levels of tumor necrosis factor (TNF)-α and transforming growth factor (TGF)-β receptor mRNA were significantly higher in Ctns−/− peritoneal Mφ compared to Ctns+/+ Mφ after incubation with apoptotic tubular cells for 24 hours (FIG. 16A). Similar cytokine differences were observed in Ctns−/− kidneys 14 days after UUO compared to Ctns+/+ kidneys (FIG. 16B).

Example 11

Plasma Cysteamine Levels in High Dose Cysteamine Bitartrate Treated Mice

Since the doses of cysteamine bitartrate (400 mg/kg and 600 mg/kg) administered to mice in Examples 1-8 were much larger compared to typical doses in humans, the serum cysteamine levels of cysteamine bitartrate were measured in the mice.

Plasma cysteamine levels were measured by mass spectrometry by the reference laboratory at UC San Diego that also runs most of the human samples for the North American patients with cystinosis. Plasma levels of cysteamine taken at the time of sacrifice were low in the 400 mg/kg and 600 mg/kg cysteamine bitartrate treated mice at day 14 after UUO (400 mg/kg−0.81±0.091 Ilmole/L; and 600 mg/kg−1.04±0.151 Ilmole/L; levels were undetectable in the vehicle alone group).

Figure 17:
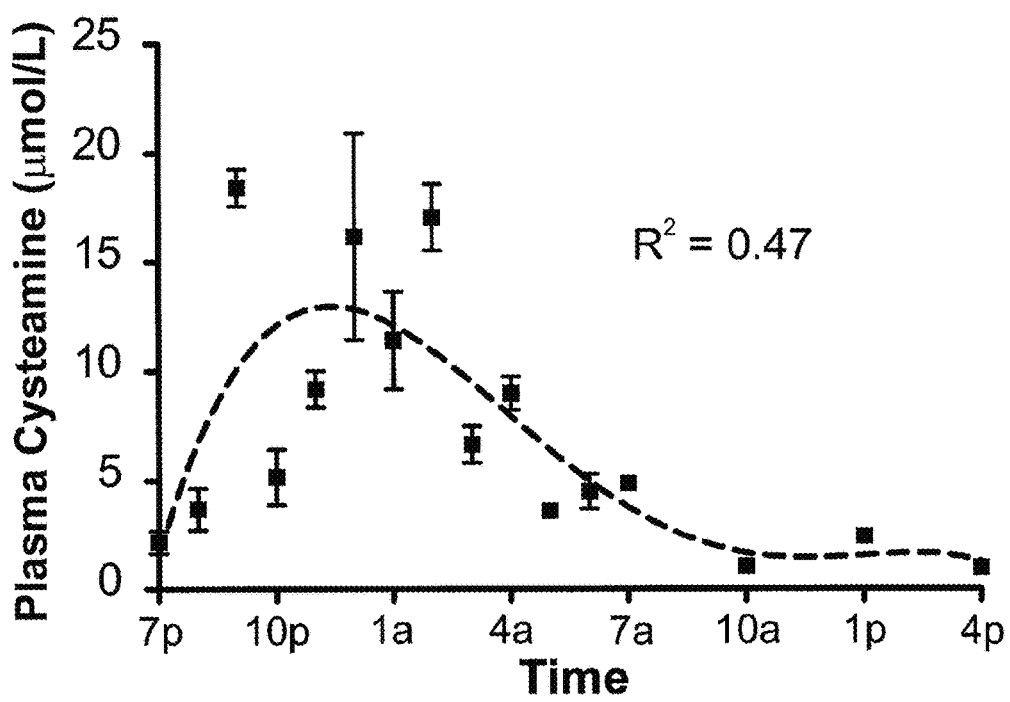
FIG. 17 shows a graph depicting plasma cysteamine levels in high dose (600 mg/kg) cysteamine bitartrate treated mice.

To test if the low levels of plasma cysteamine were attributable to the short half life of cysteamine or the nocturnal feeding habits of the mice, a more detailed analysis on the high dose cysteamine bitartrate group (600 mg/kg) was performed. C57BL/6 mice were placed on 600 mg/kg of cysteamine bitartrate in their drinking water, changed daily, for 3 days prior to sacrifice. It was assumed that an average 25 g mouse drinks 5 mLs of water per day; cysteamine bitartrate was diluted in water and prepared daily to provide 600 mg/kg. Plasma levels were taken every hour during the evening (for 12 hours) and every four hours during the day (n=4/group). Pharmacokinetic data confirms that the higher serum levels of cysteamine are achieved at night and lower levels during the day (FIG. 17). In addition, Cmax levels in mice were found to be between 15-20 μmol/L, which is similar to the levels reported in humans (Dohil R et al., J Pediatr, 2006, 148:718-9).

Example 12

Method of Treating CKD in a Human Patient by Administration of Cysteamine

A human patient suffering from Stage 1 CKD is identified. An effective dose, as determined by the physician, of cysteamine is administered to the patient. Renal function and histology is observed in the patient. Treatment is determined to be effective if minimal decrease in renal function is observed over a time period determined by the physician.

Example 13

Method of Treating a Human Patient at Risk for Developing CKD by Administration of Cysteamine A human patient with a risk factor for developing CKD is identified. The patient is given one-quarter of a maintenance dose of cysteamine bitartrate in four divided doses administered every 6 to 8 hours. The administered dose is raised gradually over four to six weeks until a maintenance dose is reached. A maintenance dosage is administered to the patient over a time period determined by the physician. Renal function and histology is observed in the patient. Treatment is determined to be effective if no decrease in renal function is observed over a time period determined by the physician.

Example 14

Method of Treating Injury-Induced CKD in a Human Patient by Administration of Cysteamine A human patient with a recent kidney trauma is identified. An effective dose, as determined by the physician, of cysteamine bitartrate is administered to the patient. Renal function and histology is observed in the patient. Treatment is determined to be effective if no decrease in renal function or interstitial fibrosis is observed over a time period determined by the physician.

Example 15

Method of Treating Cardiac Fibrosis in a Human Patient by Administration of Cysteamine A human patient with a recent cardiac infarction is identified. Cysteamine bitartrate enteric-coated is administered to the patient in effective dose determined by the physician twice daily for a time period determined by the physician. Cardiac output and histology is observed in the patient. Treatment is determined to be effective if no decrease in cardiac output is observed over a time period determined by the physician.

Example 16

Method of Treating Liver Fibrosis in a Human Patient by Administration of Cysteamine A human patient suffering from liver fibrosis is identified. Cysteamine bitartrate enteric-coated is administered to the patient in effective dose determined by the physician twice daily for a time period determined by the physician. Liver function and histology is observed in the patient. Treatment is determined to be effective if cirrhosis of the liver does not develop during a time period determined by the physician.

Example 17

Method of Treating a Human Hepatitus Patient by Administration of Cysteamine

A human patient suffering from hepatitis is identified. An effective dose, as determined by the physician, of cysteamine is administered to the patient for a period of time determined by the physician. Liver function and histology is observed in the patient. Treatment is determined to be effective if cirrhosis of the liver does not develop during a time period determined by the physician.

Example 18

Method of Treating Interstitial Lung Disease in a Human Patient by Administration of Cysteamine A human patient suffering from interstitial lung disease is identified. An effective dose, as determined by the physician, of cysteamine is administered to the patient for a period of time determined by the physician. Respiratory function and histology is observed in the patient. Treatment is determined to be effective if an increase in respiratory function is observed over a time period determined by the physician.

Example 19

Method of Treating CKD in a Human Patient by Administration of Cystamine

A human patient suffering from Stage 1 CKD is identified. An effective dose, as determined by the physician, of cystamine is administered to the patient. Renal function and histology is observed in the patient. Treatment is determined to be effective if minimal decrease in renal function is observed over a time period determined by the physician.

Example 20

Method of Treating a Human Patient at Risk for Developing CKD by Administration of Cystamine A human patient with a risk factor for developing CKD is identified. The patient is given one-quarter of a maintenance dose of cystamine in four divided doses administered every 6 to 8 hours. The administered dose is raised gradually over four to six weeks until a maintenance dose is reached. A maintenance dosage is administered to the patient over a time period determined by the physician. Renal function and histology is observed in the patient. Treatment is determined to be effective if no decrease in renal function is observed over a time period determined by the physician.

Example 21

Method of Treating Injury-Induced CKD in a Human Patient by Administration of Cystamine A human patient with a recent kidney trauma is identified. An effective dose, as determined by the physician, of cystamine is administered to the patient. Renal function and histology is observed in the patient. Treatment is determined to be effective if no decrease in renal function or interstitial fibrosis is observed over a time period determined by the physician.

What is claimed is:

1. A method of treating a fibrotic disease in a patient in need thereof, the method comprising orally administering to the patient an effective amount of enterically coated cysteamine bitartrate, to treat the fibrotic disease, wherein the fibrotic disease is atherosclerosis, asthma, cardiac fibrosis, organ transplant fibrosis, colloid and hypertrophic scar, muscle fibrosis, pancreatic fibrosis, bone-marrow fibrosis, cirrhosis of gallbladder, scleroderma, pulmonary fibrosis, diffuse parenchymal lung disease, idiopathic interstitial fibrosis, interstitial pneumonitis, desquamative interstitial pneumonia, respiratory bronchiolitis, interstitial lung disease, acute interstitial pneumonitis, nonspecific interstitial pneumonia, cryptogenic organizing pneumonia, lymphocytic interstitial pneumonia, or chronic kidney disease.

2. The method of claim 1, wherein the effective amount of cysteamine bitartrate is from 100 milligrams to 2 grams per day.

3. A method of treating a fibrotic disease in a patient in need thereof, the method comprising orally administering to the patient an effective amount of enterically coated cysteamine bitartrate, to treat the fibrotic disease, wherein the fibrotic disease is renal fibrosis.

4. The method of claim 1, wherein the fibrotic disease is cardiac fibrosis.

5. The method of claim 1, wherein the fibrotic disease is interstitial lung disease.

6. A method for treating a disorder associated with elevated levels of interstitial extracellular matrix in a tissue in a patient in need thereof, the method comprising orally administering to the patient an effective amount of enterically coated cysteamine bitartrate to treat the disorder associated with elevated levels of interstitial extracellular matrix in a tissue, wherein the disorder is atherosclerosis, asthma, cardiac fibrosis, organ transplant fibrosis, colloid and hypertrophic scar, muscle fibrosis, pancreatic fibrosis, bone-marrow fibrosis, cirrhosis of gallbladder, scleroderma, pulmonary fibrosis, diffuse parenchymal lung disease, idiopathic interstitial fibrosis, interstitial pneumonitis, desquamative interstitial pneumonia, respiratory bronchiolitis, interstitial lung disease, acute interstitial pneumonitis, nonspecific interstitial pneumonia, cryptogenic organizing pneumonia, lymphocytic interstitial pneumonia, or chronic kidney disease.

7. The method of claim 6, wherein the effective amount of cysteamine bitartrate is from 1 mg to 200 mg per kilogram of body weight daily.

8. The method of claim 6, wherein the tissue comprises an organ selected from the group consisting of lung, heart, blood vessel, gallbladder, kidney, skin, lung, muscle, pancreas, and thyroid.

9. A method for treating chronic kidney disease in a patient in need thereof, the method comprising orally administering to the patient an effective amount of enterically coated cysteamine bitartrate to treat the chronic kidney disease.

10. The method of claim 9, wherein the effective amount of cysteamine bitartrate is from 1 mg to 200 mg per kilogram of body weight daily.

11. The method of claim 9, wherein the chronic kidney disease is Stage I chronic kidney disease, Stage II chronic kidney disease, Stage III chronic kidney disease, or Stage IV chronic kidney disease.

12. The method of claim 9, wherein the chronic kidney disease is Stage I chronic kidney disease.

13. The method of claim 9, wherein the chronic kidney disease is characterized by renal fibrosis, glomerulosclerosis, tubulointerstitial fibrosis, or a combination thereof.

14. A method of ameliorating progressive interstitial fibrosis in a patient in need thereof, the method comprising orally administering to the patient an effective amount of enterically coated cysteamine bitartrate to ameliorate the progress of interstitial fibrosis, wherein the progressive interstitial fibrosis is atherosclerosis, asthma, cardiac fibrosis, organ transplant fibrosis, colloid and hypertrophic scar, muscle fibrosis, pancreatic fibrosis, bone-marrow fibrosis, cirrhosis of gallbladder, scleroderma, pulmonary fibrosis, diffuse parenchymal lung disease, idiopathic interstitial fibrosis, interstitial pneumonitis, desquamative interstitial pneumonia, respiratory bronchiolitis, interstitial lung disease, acute interstitial pneumonitis, nonspecific interstitial pneumonia, cryptogenic organizing pneumonia, lymphocytic interstitial pneumonia, or chronic kidney disease.

15. The method of claim 14, wherein the effective amount of cysteamine bitartrate is from 1 mg to 200 mg per kilogram of body weight daily.

16. The method of claim 14, wherein the patient is at risk for developing chronic kidney disease.

17. The method of claim 14, wherein the interstitial fibrosis is fibrosis of the lung, heart, blood vessel, gallbladder, kidney, skin, lung, muscle, pancreas, eye, adrenal gland, or thyroid.

18. The method of claim 1, wherein the fibrotic disease is atherosclerosis.

19. The method of claim 1, wherein the fibrotic disease is asthma.

20. The method of claim 1, wherein the fibrotic disease is organ transplant fibrosis.

21. The method of claim 1, wherein the fibrotic disease is colloid and hypertrophic scar.

22. The method of claim 1, wherein the fibrotic disease is muscle fibrosis.

23. The method of claim 1, wherein the fibrotic disease is pancreatic fibrosis.

24. The method of claim 1, wherein the fibrotic disease is bone-marrow fibrosis.

25. The method of claim 1, wherein the fibrotic disease is cirrhosis of gallbladder.

26. The method of claim 1, wherein the fibrotic disease is scleroderma.

27. The method of claim 1, wherein the fibrotic disease is pulmonary fibrosis.

28. The method of claim 1, wherein the fibrotic disease is diffuse parenchymal lung disease.

29. The method of claim 1, wherein the fibrotic disease is idiopathic interstitial fibrosis.

30. The method of claim 1, wherein the fibrotic disease is interstitial pneumonitis.

31. The method of claim 1, wherein the fibrotic disease is desquamative interstitial pneumonia.

32. The method of claim 1, wherein the fibrotic disease is respiratory bronchiolitis.

33. The method of claim 1, wherein the fibrotic disease is interstitial lung disease.

34. The method of claim 1, wherein the fibrotic disease is acute interstitial pneumonitis.

35. The method of claim 1, wherein the fibrotic disease is nonspecific interstitial pneumonia.

36. The method of claim 1, wherein the fibrotic disease is cryptogenic organizing pneumonia.

37. The method of claim 1, wherein the fibrotic disease is lymphocytic interstitial pneumonia.

38. The method of claim 1, wherein the fibrotic disease is chronic kidney disease.

39. A method for treating a disorder associated with elevated levels of interstitial extracellular matrix in a tissue in a patient in need thereof, the method comprising orally administering to the patient an effective amount of enterically coated cysteamine bitartrate to treat the disorder associated with elevated levels of interstitial extracellular matrix in a tissue, wherein the disorder is renal fibrosis.

40. The method of claim 6, wherein the disorder is cardiac fibrosis.

41. The method of claim 6, wherein the disorder is interstitial lung disease.

42. The method of claim 6, wherein the disorder is atherosclerosis.

43. The method of claim 6, wherein the disorder is asthma.

44. The method of claim 6, wherein the disorder is organ transplant fibrosis.

45. The method of claim 6, wherein the disorder is colloid and hypertrophic scar.

46. The method of claim 6, wherein the disorder is muscle fibrosis.

47. The method of claim 6, wherein the disorder is pancreatic fibrosis.

48. The method of claim 6, wherein the disorder is bone-marrow fibrosis.

49. The method of claim 6, wherein the disorder is cirrhosis of gallbladder.

50. The method of claim 6, wherein the disorder is scleroderma.

51. The method of claim 6, wherein the disorder is pulmonary fibrosis.

52. The method of claim 6, wherein the disorder is diffuse parenchymal lung disease.

53. The method of claim 6, wherein the disorder is idiopathic interstitial fibrosis.

54. The method of claim 6, wherein the disorder is interstitial pneumonitis.

55. The method of claim 6, wherein the disorder is desquamative interstitial pneumonia.

56. The method of claim 6, wherein the disorder is respiratory bronchiolitis.

57. The method of claim 6, wherein the disorder is interstitial lung disease.

58. The method of claim 6, wherein the disorder is acute interstitial pneumonitis.

59. The method of claim 6, wherein the disorder is nonspecific interstitial pneumonia.

60. The method of claim 6, wherein the disorder is cryptogenic organizing pneumonia.

61. The method of claim 6, wherein the disorder is lymphocytic interstitial pneumonia.

62. The method of claim 6, wherein the disorder is chronic kidney disease.

63. A method of ameliorating progressive interstitial fibrosis in a patient in need thereof, the method comprising orally administering to the patient an effective amount of enterically coated cysteamine bitartrate to ameliorate the progress of interstitial fibrosis, wherein the fibrotic disease is renal fibrosis.

64. The method of claim 14, wherein the progressive interstitial fibrosis is cardiac fibrosis.

65. The method of claim 14, wherein the progressive interstitial fibrosis is interstitial lung disease.

66. The method of claim 14, wherein the progressive interstitial fibrosis is atherosclerosis.

67. The method of claim 14, wherein the progressive interstitial fibrosis is asthma.

68. The method of claim 14, wherein the progressive interstitial fibrosis is organ transplant fibrosis.

69. The method of claim 14, wherein the progressive interstitial fibrosis is colloid and hypertrophic scar.

70. The method of claim 14, wherein the progressive interstitial fibrosis is muscle fibrosis.

71. The method of claim 14, wherein the progressive interstitial fibrosis is pancreatic fibrosis.

72. The method of claim 14, wherein the progressive interstitial fibrosis is bone-marrow fibrosis.

73. The method of claim 14, wherein the progressive interstitial fibrosis is cirrhosis of gallbladder.

74. The method of claim 14, wherein the progressive interstitial fibrosis is scleroderma.

75. The method of claim 14, wherein the progressive interstitial fibrosis is pulmonary fibrosis.

76. The method of claim 14, wherein the progressive interstitial fibrosis is diffuse parenchymal lung disease.

77. The method of claim 14, wherein the progressive interstitial fibrosis is idiopathic interstitial fibrosis.

78. The method of claim 14, wherein the progressive interstitial fibrosis is interstitial pneumonitis.

79. The method of claim 14, wherein the progressive interstitial fibrosis is desquamative interstitial pneumonia.

80. The method of claim 14, wherein the progressive interstitial fibrosis is respiratory bronchiolitis.

81. The method of claim 14, wherein the progressive interstitial fibrosis is interstitial lung disease.

82. The method of claim 14, wherein the progressive interstitial fibrosis is acute interstitial pneumonitis.

83. The method of claim 14, wherein the progressive interstitial fibrosis is nonspecific interstitial pneumonia.

84. The method of claim 14, wherein the progressive interstitial fibrosis is cryptogenic organizing pneumonia.

85. The method of claim 14, wherein the progressive interstitial fibrosis is lymphocytic interstitial pneumonia.

86. The method of claim 14, wherein the progressive interstitial fibrosis is chronic kidney disease.

\* \* \* \* \*